United States Patent
Maejima et al.

(10) Patent No.: US 11,046,803 B2
(45) Date of Patent: Jun. 29, 2021

(54) BLOCK COPOLYMER AND SURFACE TREATMENT AGENT USING SAME

(71) Applicant: TOSOH CORPORATION, Yamaguchi (JP)

(72) Inventors: Yukie Maejima, Mie (JP); Satoru Kondou, Mie (JP); Shinya Imatomi, Kanagawa (JP); Satoru Yamada, Kanagawa (JP); Hiroyuki Ito, Kanagawa (JP)

(73) Assignee: TOSOH CORPORATION, Yamaguchi (JP)

(*) Notice: Subject to any disclaimer, the term of this patent is extended or adjusted under 35 U.S.C. 154(b) by 12 days.

(21) Appl. No.: 16/322,361

(22) PCT Filed: Jul. 28, 2017

(86) PCT No.: PCT/JP2017/027450
§ 371 (c)(1),
(2) Date: Jan. 31, 2019

(87) PCT Pub. No.: WO2018/025767
PCT Pub. Date: Feb. 8, 2018

(65) Prior Publication Data
US 2019/0194376 A1    Jun. 27, 2019

(30) Foreign Application Priority Data
Nov. 24, 2016  (JP) .............................. JP2016-228031

(51) Int. Cl.
| | | |
|---|---|---|
| C08F 299/02 | (2006.01) | |
| C08F 293/00 | (2006.01) | |
| C08G 81/02 | (2006.01) | |
| C08F 20/18 | (2006.01) | |
| C08F 20/56 | (2006.01) | |
| C12N 5/00 | (2006.01) | |
| C12M 3/00 | (2006.01) | |
| C08G 61/02 | (2006.01) | |

(52) U.S. Cl.
CPC .......... *C08F 299/024* (2013.01); *C08F 20/18* (2013.01); *C08F 20/56* (2013.01); *C08F 293/00* (2013.01); *C08G 61/025* (2013.01); *C08G 81/02* (2013.01); *C08G 81/024* (2013.01); *C12M 3/00* (2013.01); *C12N 5/0068* (2013.01); *C08G 2261/126* (2013.01); *C08G 2261/143* (2013.01); *C08G 2261/1424* (2013.01); *C08G 2261/76* (2013.01); *C12N 2533/30* (2013.01)

(58) Field of Classification Search
CPC ...... C08F 20/56; C08F 299/024; C08F 20/18; C08F 20/54; C08F 2438/03; C08F 293/005; C08F 293/00; C08G 2261/143; C08G 2261/1424; C08G 2261/126; C12N 2533/30
See application file for complete search history.

(56) References Cited

U.S. PATENT DOCUMENTS

2008/0234391 A1   9/2008  McCormick et al.
2015/0366719 A1*  12/2015 Levinson ............ A61F 13/0233
                                                   604/307

OTHER PUBLICATIONS

Banerjee et al., Functional Group-Dependent Self-Assembled Nanostructures from Thermo-Responsive Triblock Copolymers, Langmuir 2014, 30, 4137-4146.*
Xu et al., Versatile RAFT dispersion polymerization in cononsolvents for the synthesis of thermoresponsive nanogels with controlled composition, functionality and architecture, Polym. Chem., 2014, 5, 6244-6255.*
Ll, Quanlong et al., "Doubly thermo-responsive ABC triblock copolymer nanoparticles prepared through dispersion RAFT polymerization", Polymer Chemistry, 2014, pp. 2961-2972, vol. 5, No. 8.
Qu, Yaqing et al., "In situ synthesis of thermo-responsive ABC triblock terpolymer nano-objects by seeded RAFT polymerization", Polymer Chemistry, 2014, pp. 5569-5577, vol. 5, No. 19.
Urbani, Carl N. et al., "RAFT-Mediated Emulsion Polymerization of Styrene in Water using a Reactive Polymer Nanoreactor", Australian Journal of Chemistry, 2009, pp. 528-1532, vol. 62, No. 11.
Valade, David et al., "Influence of thr Z-Group on the RAFT-Mediated Polymerizations in Nanoreactors", Journal of Polymer Science. Part A. Polymer Chemistry, 2012, pp. 762-4771, vol. 50, No. 22.
Huang,Youke et al., "Synthesis of Silica Particles Grafted with Well-Defined Living Polymeric Chains by Combination of RAFT Polymerization and Coupling Reaction", Macromolecules, 2009, pp. 5509-5517, vol. 42, No. 15.
Huang,Youke et al., "Synthesis of silica-polymer hybrids by combination of RAFT polymerization and azide-alkyne cycloaddition 'click' reactions,", Polymer Chemistry, 2010, pp. 1615-1623, vol. 1, No. 10.
Official Communication issued in WIPO Patent Application No. PCT/JP2017/027450, dated Oct. 24, 2017.

* cited by examiner

*Primary Examiner* — Jeffrey C Mullis
(74) *Attorney, Agent, or Firm* — Greenblum & Bernstein, P.L.C.

(57) ABSTRACT

The present invention addresses the problem of providing a block copolymer which is useful as a surface treatment agent for cell culture substrates, said surface treatment agent enabling cell separation in a short period of time. The above-mentioned problem is solved by a block copolymer that includes the following blocks (A), (B) and (C): (A) a temperature-responsive polymer block that has a lower critical solution temperature (LCST) within the range of from 0° C. to 50° C. with respect to water (B) a hydrophilic polymer block that does not have an LCST within the range of from 0° C. to 50° C., while having an HLB value within the range of from 9 (inclusive) to 20 (exclusive) (C) a hydrophobic polymer block that does not have an LCST within the range of from 0° C. to 50° C., while having an HLB value within the range of from 0 (inclusive) to 9 (exclusive).

13 Claims, No Drawings

BLOCK COPOLYMER AND SURFACE TREATMENT AGENT USING SAME

FIELD

The present invention relates to a block copolymer which is useful as a surface treatment agent for cell culture substrates and which enables cell separation in a short period of time.

BACKGROUND

Cell culture is used for the investigation of biochemical phenomena and the production of useful substances. Recently, with the discovery of stem cells and the progress of culture technology, significant attention has been paid to treatments using cells, including regenerative medicine.

It is known that many cells derived from mammals have adhesive properties and adhere to biological macromolecules such as collagen, fibronectin, laminin, etc., to proliferate and differentiate in the body. Similarly, in cell culture, it is necessary to adhere most cells having adhesiveness to some sort of substrate for cultivation. Conventionally, surface-treated glass or polymers have been used as substrates. For example, there are substrates in which polystyrene is irradiated with γ rays or is silicone coated. Furthermore, substrates coated with a biopolymer such as collagen or fibronectin have also been used.

In general, in the subculture of animal cells having adhesiveness as described above, an operation is performed in which cells grown on a substrate are treated with a proteolytic enzyme, detached from the substrate, and seeded on a new substrate. Proteolytic enzymes degrade proteins on cell surfaces and play a role in severing the bonds between the cell and the substrate and the bonds between cells. However, it is known that proteolytic enzymes greatly affect the survival rate of cells, and methods of separating cells from a substrate without the use of proteolytic enzymes are important as methods which do not damage cells. In regenerative medicine, it is necessary to detach the cells from the substrate without damaging the cells cultured in vitro, such as on substrates, and return the cells to a living body. Thus, there is a demand for a method of separating cells from a substrate without the use of proteolytic enzymes.

In order to solve the above problem, PTL 1 discloses a cell culture substrate in which a temperature-responsive polymer is applied to the substrate surface. In such a substrate, the adhesiveness of the substrate surface is weakened by the sol transition of the temperature-responsive polymer due to a reduction in temperature of the surrounding environment, whereby the cells can be detached and recovered. Conventionally, cells of mammalian origin are often cultured around body temperature of 37° C., and thus, a substrate from which cells can be detached below body temperature after culture has completed is required.

PTL 2 and 3 describe temperature-responsive polymers having a lower critical solution temperature (LCST) in water within the range below body temperature. Examples thereof include poly(N-isopropylacrylamide) (LCST=32° C.), poly(N-n-propylacrylamide) (LCST=21° C.), poly(N-n-propylmethacrylamide) (LCST=32° C.), poly(N-ethoxyethylacrylamide) (LCST=about 35° C.), poly(N-tetrahydrofurfuryl acrylamide) (LCST=about 28° C.), poly(N-tetrahydrofurfurylmethacrylamide) (LCST=about 35° C.), and poly(N,N-diethylacrylamide) (LCST=32° C.) (PTL 2 and 3).

When the above temperature-responsive polymers are used on a cell culture substrate, it is necessary to lower the temperature of the cell culture substrate below the lower critical solution temperature, and depending on the amount of time necessary, the temperature of the cells may be lowered at the same time. A reduction in cell temperature reduces cell activity. Thus, it is necessary to shorten the cooling time.

CITATION LIST

Patent Literature

[PTL 1] Japanese Unexamined Patent Publication (Kokai) No. H2-211865
[PTL 2] Japanese Unexamined Patent Publication (Kokai) No. H3-266980
[PTL 3] Japanese Unexamined Patent Publication (Kokai) No. H5-244938

SUMMARY

Technical Problem

The object of the present invention is to provide a block copolymer which is useful as a surface treatment agent for cell culture substrates that enables cell separation in a short period of time and a surface treatment agent using the same.

Solution to Problem

In light of the above points, the present inventors have discovered, as a result of rigorous investigation, that coating a substrate with a block copolymer comprising a temperature-responsive polymer, a hydrophilic polymer, and a hydrophobic polymer to form a membrane enables cell separation in a short time, and have achieved the present invention.

Specifically, the present invention encompasses the Aspects described in [1] to [19] below.

[1] A block copolymer comprising the following blocks (A), (B), and (C):
(A) a temperature-responsive polymer block having a lower critical solution temperature (LCST) in water in the range of 0° C. to 50° C.;
(B) a hydrophilic polymer block which does not have an LCST in the range of 0° C. to 50° C. and which has an HLB value (as determined by the Griffin method) in the range of 9 to 20; and
(C) a hydrophobic polymer block which does not have an LCST in the range of 0° C. to 50° C. and which has an HLB value (as determined by the Griffin method) in the range from 0 to less than 9.

[2] The block copolymer according to [1], wherein the block (A) is a polymer comprising at least one repeating unit from among repeating units represented by the following Formula (1):

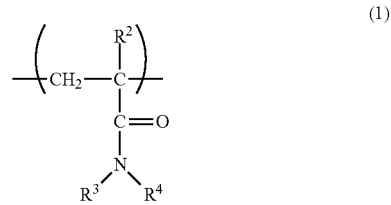

(1)

where $R^2$ is a hydrogen atom or methyl group, $R^3$ and $R^4$ are each independently a hydrogen atom, $C_{1-6}$ hydrocarbon group, $C_{2-4}$ hydrocarbon group which may be substituted with a $C_{1-2}$ alkyloxy group, $C_{2-4}$ hydrocarbon group which may be substituted with fluorine, furfuryl group, or tetrahydrofurfuryl group, and $R^3$ and $R^4$ may be connected to form a pyrrolidine ring, piperidine ring or morpholine ring.

[3] The block copolymer according to [1], wherein the block (A) is a polymer comprising at least one repeating unit from among repeating units represented by the following Formula (2):

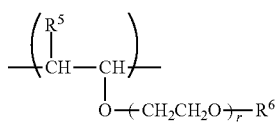

(2)

where $R^5$ is a hydrogen atom or methyl group, $R^6$ is a hydrogen atom or $C_{1-6}$ hydrocarbon group, and r is an integer from 1 to 10.

[4] The block copolymer according to [1], wherein the block (A) is a polymer comprising at least one repeating unit from among repeating units represented by the following Formula (3):

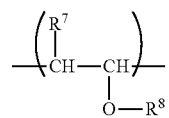

(3)

where $R^7$ is a hydrogen atom or methyl group and $R^8$ is a $C_{1-6}$ hydrocarbon group.

[5] The block copolymer according to any one of [1] to [4], wherein the block (B) is a polymer comprising at least one repeating unit from among repeating units represented by the following Formula (4):

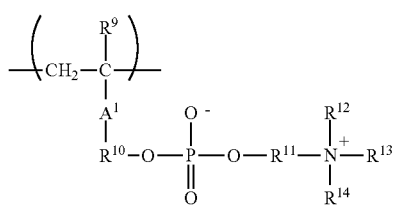

(4)

where $R^9$ is a hydrogen atom or methyl group, $R^{10}$ is a $C_{1-10}$ alkylene group, $R^{11}$ is a $C_{1-4}$ divalent hydrocarbon group, $R^{12}$, $R^{13}$, and $R^{14}$ are each independently a hydrogen atom, methyl group, or ethyl group, and $A^1$ is a divalent bond selected from the group consisting of an ester bond, amide bond, urethane bond, and ether bond.

[6] The block copolymer according to any one of [1] to [4], wherein the block (B) is a polymer comprising at least one repeating unit from among the repeating units represented by the following Formula (5):

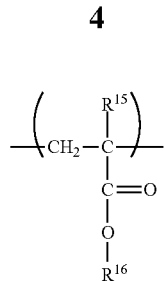

(5)

where $R^{15}$ is a hydrogen atom or methyl group and $R^{16}$ is $-(CH_2CH_2O)_i-(CH_2O)_j-(CH_2CH(CH_3)O)_k-R^{17}$ (where $R^{17}$ is a hydrogen atom or $C_{1-10}$ alkyl group, i is an integer from 1 to 30, and j and k are each independently an integer from 0 to 30).

[7] The block copolymer according to any one of [1] to [4], wherein the block (B) is a polymer comprising at least one repeating unit from among repeating units represented by the following Formula (6):

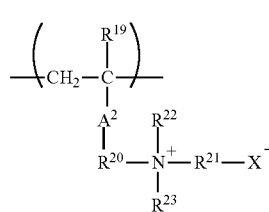

(6)

where $R^{19}$ is a hydrogen atom or methyl group. $R^{20}$ is a $C_{1-10}$ alkylene group, $R^{21}$ is a $C_{1-4}$ alkylene group, $R^{22}$ and $R^{23}$ are each independently a hydrogen atom or $C_{1-4}$ hydrocarbon group, $A^2$ is a divalent bond selected from the group consisting of an ester bond, amide bond, urethane bond, and ether bond, and X is a sulfonic acid group, carboxyl group, or phosphoric acid group.

[8] The block copolymer according to any one of [1] to [4], wherein the block (B) is a polymer comprising at least one repeating unit from among repeating units represented by the following Formula (7):

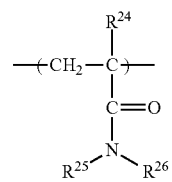

(7)

where $R^{24}$, $R^{25}$, and $R^{26}$ are each independently a hydrogen atom or methyl group.

[9] The block copolymer according to any one of [1] to [4], wherein the block (B) is a polymer comprising at least one repeating unit from among repeating units represented by the following Formula (8):

(8)

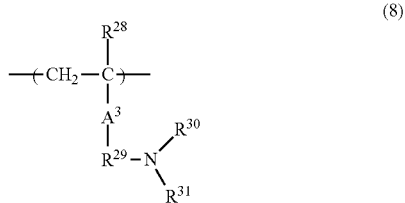

where $R^{28}$ is a hydrogen atom or methyl group. $R^{29}$ is a $C_{2-7}$ alkylene group, $R^{30}$ and $R^{31}$ are each independently a hydrogen atom, methyl group, or ethyl group, and $A^3$ is a divalent bond selected from the group consisting of an ester bond, amide bond, urethane bond, and ether bond.

[10] The block copolymer according to any one of [1] to [4], wherein the block (B) is a polymer comprising at least one repeating unit from among repeating units represented by the following Formula (9):

(9)

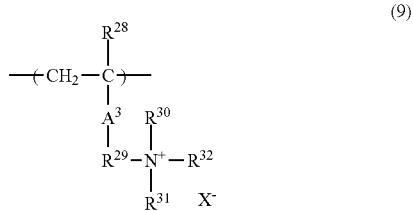

where $R^{28}$ is a hydrogen atom or methyl group, $R^{29}$ is a $C_{2-7}$ alkylene group, $R^{30}$ and $R^{31}$ are each independently a hydrogen atom, methyl group, or ethyl group, $R^{32}$ is a $C_{1-4}$ hydrocarbon group or $C_{2-4}$ hydrocarbon group which may be substituted with a hydroxyl group or $C_{1-2}$ alkyloxy group, $A^3$ is a divalent bond selected from the group consisting of an ester bond, amide bond, urethane bond, and ether bond, and $X^-$ is a halide ion, hydroxide ion, or acetate ion.

[11] The block copolymer according to any one of [1] to [10], wherein the block (C) is a polymer comprising at least one repeating group from among repeating groups represented by the following Formula (10):

(10)

where $R^{33}$ is a hydrogen atom or methyl group, and Y is a hydrogen atom, chlorine atom, acetoxy group, nitrile group, or $C_{6-30}$ aromatic hydrocarbon group.

[12] The block copolymer according to any one of [1] to [10], wherein the block (C) is a polymer comprising at least one repeating unit from among repeating units represented by the following Formula (11):

(11)

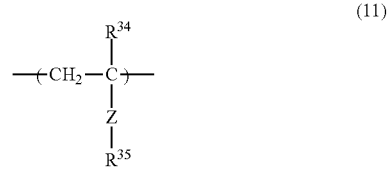

where $R^{34}$ is a hydrogen atom or methyl group, $R^{35}$ is a $C_{1-30}$ hydrocarbon group, and Z is a divalent bond selected from the group consisting of an ester bond, amide bond, urethane bond, and ether bond.

[13] The block copolymer according to any one of [1] to [12], wherein block (A), block (B), and block (C) constituting the block copolymer have the following mol % (a) to (c) with respect to the total thereof, respectively:
  (a) the ratio of block (A) is 25 mol % to 85 mol %;
  (b) the ratio of block (B) is 2 mol % to 50 mol %; and
  (c) the ratio of block (C) is 10 mol % to 70 mol %.

[14] The block copolymer according to any one of [1] to [13], wherein the number average molecular weight (Mn) of the block copolymer is in the range of 3,000 to 1,000,000.

[15] The block copolymer according to any one of [1] to [14], comprising at least one bond via a spacer between blocks (A), (B), and (C), wherein at least one of the bonds via the spacer is a divalent bond comprising at least one bond from among divalent bonds represented by the following Formulae (12) and (13):

(12)

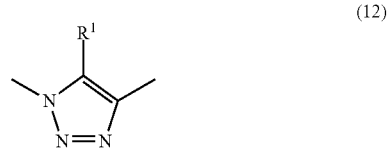

(13)

where $R^1$ is a hydrogen atom or $C_{1-20}$ hydrocarbon group.

[16] A method for the production of the block copolymer according to any one of 11 to [15], comprising the following steps (1) to (3):
  (1) producing any one of the blocks from among blocks (A), (B), and (C) according to [1];
  (2) producing a partial block copolymer comprising the block produced in step (1) and, connected thereto, one of the blocks from among blocks (A), (B), and (C) according to [1] except the block produced in step (1); and
  (3) producing a block copolymer comprising the partial block copolymer produced in step (2) and, connected thereto, the block among blocks (A), (B), and (C) according to [1] which does not constitute a block copolymer comprising the partial block copolymer produced in step (2).

[17] A surface treatment agent for substrates, comprising the block copolymer according to any one of [1] to [15].

[18] A membrane comprising the surface treatment agent according to [17] applied to a substrate.

[19] A substrate for cell culture having a surface coated with the membrane according to [18].

[20] A cell culture method, comprising culturing, using the cell culture substrate according to [19], a cell at a temperature higher than the LCST of the temperature-responsive polymer block according to [1], and after cell proliferation, lowering the temperature below the LCST to detach proliferated cells from the substrate.

Advantageous Effects of Invention

By coating a cell culture substrate with a membrane obtained from the block copolymer of the present invention, which includes a temperature-responsive polymer block, a hydrophilic polymer block, and a hydrophobic polymer block, after cell culture, hydrophilization of the substrate surface due to temperature reduction is promoted, and the cooling time necessary for cell separation can be shortened. As a result, a cell culture substrate from which cells can be recovered in a short time without damaging the cells even if a cooling treatment is applied after cell culture can be obtained.

DESCRIPTION OF EMBODIMENTS

The modes for carrying out the present invention (hereinafter referred to simply as the "embodiments") will be described in detail below. The following embodiments are merely for explaining the present invention and are not intended to limit the present invention to the following contents. Appropriate modifications can be made within the scope of the gist of the present invention.

1. Block Copolymer

The block copolymer of the present invention is a block copolymer comprising the following blocks (A), (B), and (C).

(A) A temperature-responsive polymer block having a lower critical solution temperature (LCST) in water in the range of 0° C. to 50° C.

(B) A hydrophilic polymer block which does not have an LCST in the range of 0° C. to 50° C. and which has an HLB value (as determined by the Griffin method) in the range of 9 to 20.

(C) A hydrophobic polymer block which does not have an LCST in the range of 0° C. to 50° C. and which has an HLB value (as determined by the Griffin method) in the range from 0 to less than 9.

The details of block (A), block (B), and block (C) of the present invention will be described below. Note that the term "polymer" encompasses the terms "copolymer" and "homopolymer". Specifically, the repeating units constituting the blocks (A), (B), and (C) may be composed of a single type or may be composed of two or more types.

Block (A) of the present invention is a temperature-responsive polymer block having an LCST in the range of 0° C. to 50° C. LCST stands for lower critical solution temperature. LCST is the temperature below which the polymer will dissolve in water to form a transparent solution, and above which the polymer becomes insoluble and causes clouding or precipitation, resulting in phase separation.

When cells are cultured using a cell culture substrate comprising the block copolymer of the present invention, which is produced by a method described later, if the LCST is less than 0° C., it is difficult to detach the cells without causing damage to the cells, and if the LCST exceeds 50° C., the cells cannot adhere near body temperature, whereby cell culture becomes difficult. Thus, it is necessary that the LCST of block (A) be in the range of 0° C. to 50° C. Cell adhesion occurs at around 37° C., which is body temperature, and cell separation occurs as a result of temperature reduction. Thus, from the viewpoint of recovering the cells without damage, the LCST of block (A) is preferably in the range of 10° C. to 40° C., more preferably in the range of 20° C. to 35° C.

The block (A) constituting the block copolymer of the present invention is not particularly limited as long as it is a polymer block having an LCST in the range of 0° C. to 50° C. Preferable examples of the repeating units constituting block (A) are the repeating units represented by the following Formulae (1) to (3). Block (A) may be composed of a single type of repeating unit or may be composed of two or more types of repeating units.

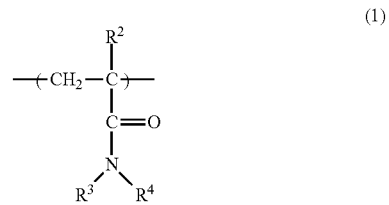

(1)

In the formula, $R^2$ is a hydrogen atom or a methyl group. From the viewpoint of obtaining an LCST in the range of 0° C. to 50° C., a hydrogen atom is preferable.

$R^3$ and $R^4$ are each independently a hydrogen atom, $C_{1-6}$ hydrocarbon group, $C_{2-4}$ hydrocarbon group which may be substituted with a $C_{1-2}$ alkyloxy group, $C_{2-4}$ hydrocarbon group which may be substituted with fluorine, furfuryl group, or tetrahydrofurfuryl group and $R^3$ and $R^4$ may be connected to form a pyrrolidine ring, piperidine ring or morpholine ring. Examples of $C_{1-6}$ hydrocarbon groups include methyl groups, ethyl groups, n-propyl groups, isopropyl groups, cyclopropyl groups, n-butyl groups, isobutyl groups, tert-butyl groups, n-hexyl groups, and isohexyl groups. Furthermore, examples of $C_{2-4}$ hydrocarbon groups which may be substituted with a $C_{1-2}$ alkyloxy group include methoxyethyl groups, ethoxyethyl groups, methoxypropyl groups, ethoxypropyl groups, methoxybutyl groups, and ethoxybutyl groups. Further, examples of $C_{2-4}$ hydrocarbon groups which may be substituted with fluorine include 2-fluoroethyl groups, 2,2-difluoroethyl groups, 2,2,2-trifluoroethyl groups, 3,3,3-trifluoropropyl groups, 2,2,3,3,3-pentafluoropropyl groups, and 2,2,3,3,4,4,4-heptafluorobutyl groups. Among these, from the viewpoint of obtaining an LCST in the range of 0° C. to 50° C., a $C_{1-6}$ hydrocarbon group is preferably used, and an n-propyl group or isopropyl group is more preferably used.

Examples of the repeating units represented by general Formula (1) of the present invention include repeating units generated by polymerizing monomers selected from N,N-diethylacrylamide, N-ethylacrylamide, N-n-propylacrylamide, N-n-propylmethacrylamide, N-isopropylacrylamide, N-isopropylmethacrylamide, N-cyclopropyl acrylamide, N-cyclopropyl methacrylamide, N-ethoxyethyl acrylamide, N-ethoxyethyl methacrylamide, N-tetrahydrofurfuryl acrylamide, N-tetrahydrofurfuryl methacrylamide, 1-(1-oxo-2-propenyl)pyrrolidine, 1-(1-oxo-2-methyl-2-propenyl) pyrrolidine, 1-(1-oxo-2-propenyl)piperidine, 1-(1-oxo-2-methyl-2-propenyl)piperidine, 4-(1-oxo-2-propenyl)morpholine, and 4-(l-oxo-2-methyl-2-propenyl)morpholine. From the viewpoint of obtaining an LCST in the range of 10° C. to 40° C., repeating units generated by polymerizing N,N-diethylacrylamide, N-n-propylacrylamide, N-isopropylacrylamide, N-n-propylmethacrylamide, N-ethoxyethylacrylamide, N-tetrahydrofurfurylacrylamide, or N-tetrahydrofurfurylmethacrylamide are preferable, and from the viewpoint of obtaining an LCST in the range of 20° C. to 35° C., repeating units generated by copolymerizing monomers selected from N,N-diethylacrylamide, N-isopropylacrylamide, N-n-propylmethacrylamide, N-ethoxyethylacrylamide, and N-tetrahydrofurfurylmethacrylamide are more preferable.

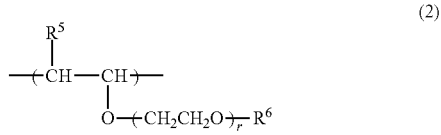

(2)

In the Formula, $R^5$ represents a hydrogen atom or a methyl group. In order to obtain an LCST in the range of 0° C. to 50° C., a hydrogen atom is used. $R^6$ is a hydrogen atom or a $C_{1-6}$ hydrocarbon group. Examples of $C_{1-6}$ hydrocarbon groups include methyl groups, ethyl groups, n-propyl groups, isopropyl groups, cyclopropyl groups, n-butyl groups, isobutyl groups, tert-butyl groups, n-hexyl groups, and isohexyl groups. From the viewpoint of obtaining an LCST in the range of 0° C. to 50° C., a $C_{1-3}$ hydrocarbon group is preferably used. r is an integer from 1 to 10, and from the viewpoint of obtaining an LCST in the range of 0° C. to 50° C., is preferably an integer from 1 to 3. Examples of the repeating units represented by Formula (2) of the present invention preferably include, in order to obtain an LCST in the range of 10° C. to 40° C., repeating units generated by polymerizing 2-ethoxyethylvinyl ether.

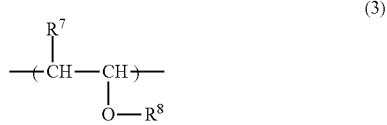

(3)

In the Formula, $R^7$ represents a hydrogen atom or a methyl group. From the viewpoint of obtaining an LCST in the range of 0° C. to 50° C., a hydrogen atom is preferably used. $R^8$ is a $C_{1-6}$ hydrocarbon group. Examples of $C_{1-6}$ hydrocarbon groups include methyl groups, ethyl groups, n-propyl groups, isopropyl groups, cyclopropyl groups, n-butyl groups, isobutyl groups, tert-butyl groups, n-hexyl groups, and isohexyl groups. From the viewpoint of obtaining an LCST in the range of 0° C. to 50° C., a methyl group or ethyl group is preferably used. Examples of the repeating units represented by Formula (3) of the present invention include, from the viewpoint of obtaining an LCST in the range of 10° C. to 40° C., repeating units generated by polymerizing methyl vinyl ether.

As the structural unit of block (A) constituting the block copolymer of the present invention, among the repeating units represented by any one of the general formulae (1) to (3), in view of good cell separability due to the temperature reduction, a repeating unit represented by the general formula (1) is preferably used.

Block (B) of the present invention is a block of a hydrophilic polymer which does not have an LCST in the range of 0° C. to 50° C. and which has an HLB value in the range of 9 to 20.

In the present description, HLB (Hydrophile-Lipophile Balance) value means the value representing the degree of affinity with water and oil, as described in W. C. Griffin, Journal of the Society of Cosmetic Chemists, 1, 311 (1949). HLB values are in the range of 0 to 20. The closer the value to 0, the higher the hydrophobicity, and the closer to 20, the higher the hydrophilicity. The HLB value may be obtained by a calculation formula in accordance with the Atlas method, the Griffin method, the Davis method, or the Kawakami method. In the present description, HLB values are calculated in accordance with the Griffin method by the following calculation formula based on the formula weight of the hydrophilic moieties of the repeating unit and the total formula quantity of the repeating unit of each block constituting the block copolymer of the present invention.

HLB value=20×(the formula weight of the hydrophilic moiety of the repeating unit)/(the total formula weight of the repeating unit).

Examples of the hydrophilic moieties in the repeating unit of each block include sulfone moieties ($-SO_3-$), phosphono group moieties ($-PO_3-$), carboxyl group moieties ($-COOH$), ester moieties ($-COO-$), amide moieties ($-CONH-$), imide moieties ($-CON-$), aldehyde group moieties ($-CHO$), carbonyl group moieties ($-CO-$), hydroxyl group moieties ($-OH$), amino group moieties ($-NH_2$), acetyl group moieties ($-COCH_3$), ethylene amine moieties ($-CH_2CH_2N-$), ethyleneoxy moieties ($-CH_2CH_2O-$), alkali metal ions, alkaline earth metal ions, ammonium ions, halide ions, and acetate ions.

In the calculation of the hydrophilic moieties in the repeating unit, the atoms constituting a hydrophilic moiety must not overlap as atoms constituting other hydrophilic moieties. Examples of the calculation of the HLB value in the repeating unit are described below. For example, in the case of 2-methacryloyloxyethyl phosphorylcholine (molecular weight: 295.27), the hydrophilic moieties include 1 ester moiety, 1 phosphono group moiety, and 1 ethyleneamine moiety, and the molecular weight of the hydrophilic moieties is 181.04. Thus, the HLB value of 2-methacryloyloxyethyl phosphorylcholine is 12.3. In the case of 2-dimethylaminoethyl methacrylate (molecular weight: 157.11), the hydrophilic moieties include 1 ester moiety and 1 ethyleneamine moiety, and the molecular weight of the hydrophilic moieties is 44.01. Thus, the HLB value of 2-dimethylaminoethyl methacrylate is 8.8. In the case of n-butyl methacrylate (molecular weight: 142.20), the hydrophilic moieties include 1 ester moiety, and the molecular weight of the hydrophilic moieties is 44.01. Thus, the HLB value of n-butyl methacrylate is 6.2.

Further, when each block constituting the block copolymer of the present invention is a copolymer comprising different monomers (monomer 1, monomer 2, etc.), the ratio (mol %) in the copolymer of the repeating unit generated by polymerization of each monomer can be analyzed and calculated by the following calculation formula.

HLB value=HLB $value_1 \times ratio_1$+HLB $value_2 \times ratio_2$+ . . .

HLB $value_1$ is the HLB value of the polymer generated by polymerizing monomer 1 and $ratio_1$ is the ratio (mol %) of the repeating unit generated by polymerizing monomer 1 in the copolymer. HLB $value_2$ is the HLB value of the polymer generated by polymerizing monomer 2 and $ratio_2$ is the ratio (mol %) of the repeating unit generated by polymerizing monomer 2 in the copolymer.

Furthermore, block (B) may include a hydrophobic monomer as long as the HLB value thereof is in the range of 9 to less than 20. For example, a copolymer comprising a monomer including the above hydrophilic group and alkyl(meth)acrylate or a styrene derivative may be used.

When block (B) of the present invention has an HLB value less than 9, as the hydrophobicity increases, the cooling time necessary for cell separation is lengthened, resulting in a decrease in cell activity. Thus, it is necessary that the HLB value be in the range of 9 to less than 20. Conversely, when the HLB value approaches 20, hydrophobicity increases, whereby cell adhesion becomes difficult. Thus, the HLB value of block (B) of the present application is preferably in the range of 9 to less than 19, more preferably 9 to less than 17.

Block (B) constituting the block copolymer of the present invention is not particularly limited as long it is a polymer block having an HLB value in the range of 9 to 20. Preferred examples of the repeating units constituting block (B) are the repeating units represented by Formulae (4) to (9) below. Block (B) may be composed of a single type of repeating unit or may be composed of two or more types of repeating units.

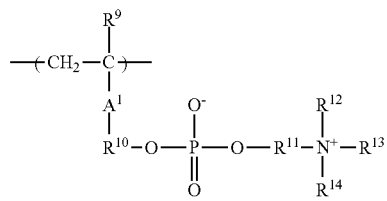
(4)

In the Formula, $R^9$ is a hydrogen atom or a methyl group. $R^{10}$ is a $C_{1-10}$ alkylene group, and from the viewpoints of controlling cell adhesiveness and shortening the cooling time necessary for cell separation, a $C_{1-6}$ alkylene group is preferable. Examples of such alkylene groups include methylene groups, ethylene groups, propylene groups, butlene groups, pentamethylene groups, and hexamethylene groups. Ethylene groups are more preferable. Furthermore, from the viewpoints of controlling cell adhesiveness and reducing the cooling time necessary for cell separation, $R^{10}$ is preferably a (poly)oxyethylene group.

$R^{11}$ is a $C_{1-4}$ divalent hydrocarbon group. From the viewpoint of reducing the cooling time necessary for cell separation, $R^{11}$ is preferably a $C_{1-4}$ alkylene group, for example, a methylene group, an ethylene group, a propylene group, or a butylene group, more preferably an ethylene group. $R^{12}$, $R^{13}$, and $R^{14}$ are each independently a hydrogen atom, methyl group, or ethyl group. From the viewpoints of controlling cell adhesiveness and reducing the cooling time necessary for cell separation, $R^{12}$, $R^{13}$, and $R^{14}$ are all preferably simultaneously a hydrogen atom or a methyl group, more preferably simultaneously a methyl group. $A^1$ is a divalent bond selected from the group consisting of an ester bond, amide bond, urethane bond, and ether bond. From the viewpoints of controlling cell adhesiveness and reducing the cooling time necessary for cell separation, $A^1$ is preferably an ester bond or an amide bond, more preferably an ester bond.

Examples of the repeating units represented by Formula (4) of the present invention include repeating units generated by polymerizing monomers selected from 2-methacryloyloxyethyl phosphorylcholine, 2-acryloyloxyethyl phosphorylcholine, 3-(meth)acryloyloxypropyl phosphorylcholine, 4-(meth)acryloyloxybutylphosphorylcholine, 6-(meth)acryloyloxyhexylphosphorylcholine, 10-(meth)acryloyloxydecylphosphorylcholine, co-(meth)acryloyl(poly)oxyethylenephosphorylcholine, 2-acrylamidoethylphosphorylcholine, 3-acrylamidopropylphosphorylcholine, 4-acrylamidobutylphosphorylcholine, 6-acrylamidohexylphosphorylcholine, 10-acrylamidodecylphosphorylcholine, and ω-(meth)acrylamide(poly)oxyethylene phosphorylcholine. Among these repeating units, from the viewpoints of controlling cell adhesiveness and reducing the cooling time necessary for cell separation, repeating units generated by polymerizing 2-methacryloyloxyethyl phosphorylcholine are preferred.

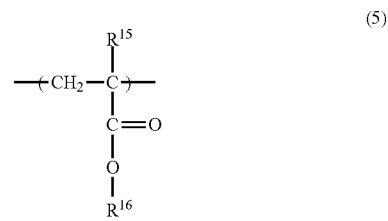
(5)

In the formula, $R^{15}$ is a hydrogen atom or methyl group. $R^{16}$ is a (poly)oxyalkylene group comprising a $C_{1-3}$ alkylene, and is represented by $-(CH_2CH_2O)_i-(CH_2O)_j-(CH_2CH(CH_3)O)_k-R^{17}$ (where $R^{17}$ is a hydrogen atom, a $C_{1-10}$ alkyl group, a furfuryl group, or a tetrahydrofurfuryl group, i is an integer from 1 to 30, and j and k are integers from 0 to 30).

Examples of repeating units represented by Formula (5) of the present invention include repeating units generated by polymerizing monomers selected from polyethylene glycol methacrylate, 2-hydroxyethyl acrylate, 2-hydroxyethyl methacrylate, hydroxymethyl acrylate, hydroxymethyl methacrylate, 2-methoxyethyl acylate, 2-methoxyethyl methacrylate, furfuryl acrylate, furfuryl methacrylate, tetrahydrofurfuryl acrylate, and tetrahydrofurfuryl methacrylate. Among these repeating units, from the viewpoints of controlling cell adhesion and reducing the cooling time necessary for cell separation, repeating units generated by polymerizing polyethylene glycol methacrylate, 2-methoxyethyl acrylate, or tetrahydrofurfuryl acrylate are preferred.

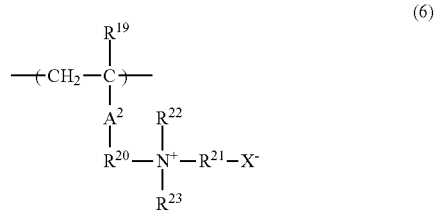
(6)

In the Formula, $R^{19}$ is a hydrogen atom or methyl group. $R^{20}$ is a $C_{1-10}$ alkylene group. From the viewpoints of controlling cell adhesion and reducing the cooling time necessary for cell separation, $R^{20}$ is preferably a $C_{1-6}$ alkylene group such as a methylene group, ethylene group, propylene group, butylene group, pentamethylene group, or hexamethylene group. An ethylene group or propylene group is more preferable.

$R^{21}$ is a $C_{1-4}$ alkylene group. From the viewpoints of controlling cell adhesion and reducing the cooling time necessary for cell separation, $R^{21}$ is preferably an alkylene group such as a methylene group, ethylene group, propylene group, or butylene group. An ethylene group or propylene group is more preferable. $R^{22}$ and $R^{23}$ are each independently a hydrogen atom or $C_{1-4}$ hydrocarbon group. From the viewpoints of controlling cell adhesion and reducing the cooling time necessary for cell separation, $R^{22}$ and $R^{23}$ are preferably simultaneously a hydrogen atom or methyl group, more preferably simultaneously a methyl group.

$A^2$ is a divalent bond selected from the group consisting of an ester bond, amide bond, urethane bond, and ether bond. From the viewpoints of controlling cell adhesiveness and reducing the cooling time necessary for cell separation, $A^2$ is preferably an ester bond or amide bond, more preferably an ester bond. Furthermore, X is a sulfonic acid group, carboxyl group, or phosphoric acid group.

Examples of repeating units represented by Formula (6) of the present invention include repeating units generated by polymerizing monomers selected from dimethyl (2-methacryloyloxyethyl) (carboxylatomethyl) aminium, dimethyl (2-methacryloyloxyethyl) (2-carboxylatoethyl) aminium, dimethyl (2-acryloyloxyethyl) (2-carboxylatoethyl) aminium, dimethyl (2-methacryloyloxyethyl) (3-carboxylatopropyl) aminium, dimethyl (2-acryloyloxyethyl) (3-carboxylatopropyl) aminium, dimethyl (3-methacryloylaminopropyl) (3-sulfonatopropyl) aminium, dimethyl (3-methacryloylamino propyl) (4-sulfonatobutyl) aminium, dimethyl (2-methacryloyloxyethyl) (2-sulfonatoethyl) aminium, dimethyl (2-acryloyloxyethyl) (2-sulfonatoethyl) aminium, dimethyl (2-methacryloyloxyethyl) (3-sulfonatopropyl) aminium, dimethyl (2-acryloyloxyethyl) (3-sulfonatopropyl) aminium, dimethyl (2-methacryloyloxyethyl) (2-phosphonatomethyl) aminium, dimethyl (2-acryloyloxyethyl) (2-phosphonatomethyl) aminium, dimethyl (2-methacryloyloxyethyl) (3-phosphonatopropyl) aminium, and dimethyl (2-acryloyloxyethyl) (3-phosphonatopropyl) aminium. From the viewpoints of controlling cell adhesiveness and reducing the cooling time necessary for cell separation, repeating units generated by polymerizing dimethyl (2-methacryloyloxyethyl) (carboxylatomethyl) aminium, dimethyl (2-methacryloyloxyethyl) (2-carboxylatoethyl) aminium, dimethyl (3-methacryloylaminopropyl) (3-sulfonatopropyl) aminium, dimethyl (3-methacryloylaminopropyl) (4-sulfonatobutyl) aminium, or dimethyl (2-methacryloyloxyethyl) (2-sulfonatoethyl) aminium are preferred.

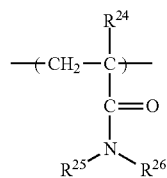

(7)

In the Formula, $R^{24}$ is a hydrogen atom or methyl group. $R^{25}$ and $R^{26}$ are each independently a hydrogen atom or methyl group.

Examples of repeating units represented by Formula (7) of the present invention include repeating units generated by polymerizing acrylamide or N,N-dimethylacrylamide.

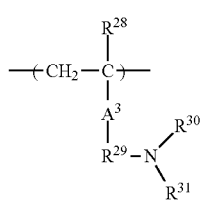

(8)

In the Formula, $R^{28}$ is a hydrogen atom or methyl group. From the viewpoints of controlling cell adhesiveness and reducing the cooling time necessary for cell separation, $R^{28}$ is preferably a methyl group. $R^{29}$ is a $C_{2-7}$ alkylene group. From the viewpoints of controlling cell adhesiveness and reducing the cooling time necessary for cell separation, $R^{29}$ is preferably a $C_{2-4}$ alkylene group, more preferably an ethylene group. $R^{30}$ and $R^{31}$ are each independently a hydrogen atom, methyl group, or ethyl group. From the viewpoints of controlling cell adhesiveness and reducing the cooling time necessary for cell separation $R^{30}$ and $R^{31}$ are preferably simultaneously a hydrogen group or methyl group, more preferably simultaneously a methyl group. $A^3$ is a divalent bond selected from the group consisting of an amide bond, urethane bond, and ether bond. From the viewpoints of controlling cell adhesiveness and reducing the cooling time necessary for cell separation, $A^3$ is preferably an ester bond or an amide bond, more preferably an ester bond.

Examples of repeating units represented by Formula (8) of the present invention include repeating units generated by polymerizing aminoethyl(meth)acrylate, 2-dimethylaminoethyl (meth)acrylate, 2-diethylaminoethyl (meth)acrylate, 3-aminopropyl (meth)acrylate, 3-dimethylaminopropyl (meth)acrylate, 3-diethylaminopropyl (meth)acrylate, (meth)acrylamidoethylamine, dimethyl [(meth)acrylamidoethyl] amine, diethyl [(meth)acrylamidoethyl] amine, 3-(meth)acrylamidopropylamine, dimethyl [3-(meth)acrylamidopropyl] amine, or diethyl [3-(meth)acrylamidopropyl] amine as a monomer. From the viewpoints of controlling cell adhesiveness and reducing the cooling time necessary for cell separation, repeating units generated by polymerizing 2-dimethylaminomethyl (meth)acrylate, 2-dimethylaminoethyl (meth)acrylate, dimethyl [(meth)acrylamidomethyl]amine, or dimethyl [(meth)acrylamidoethyl] amine are preferred.

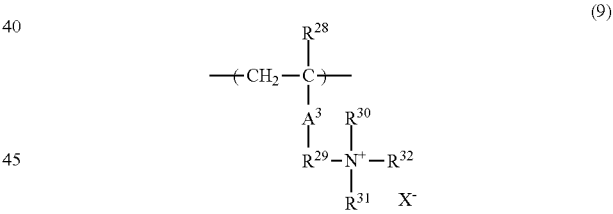

(9)

In the Formula. $R^{28}$ is a hydrogen atom or methyl group. From the viewpoints of controlling cell adhesiveness and reducing the cooling time necessary for cell separation, $R^{28}$ is preferably a methyl group. $R^{29}$ is a $C_{2-7}$ alkylene group. From the viewpoints of controlling cell adhesiveness and reducing the cooling time necessary for cell separation, $R^{29}$ is preferably a $C_{2-4}$ alkylene group, more preferably an ethylene group. $R^{30}$ and $R^{31}$ are each independently a hydrogen atom, methyl group, or ethyl group. From the viewpoint of reducing the cooling time necessary for cell separation, $R^{30}$ and $R^{31}$ are preferably simultaneously a hydrogen atom or methyl group, preferably simultaneously a methyl group. $R^{32}$ is a $C_{1-4}$ hydrocarbon group or $C_{2-4}$ hydrocarbon group which may be substituted with a hydroxyl group or $C_{1-2}$ alkyloxy group. From the viewpoint of reducing the cooling time necessary for cell separation, $R^{32}$ is preferably an ethylene group which may be substituted with a methyl group, ethyl group, hydroxyl group, or methoxy group. $A^3$ is a divalent bond selected from the group consisting of an ester bond, amide bond, urethane bond, and ethyl bond. From the viewpoints of controlling cell adhesiveness and reducing the cooling time necessary for cell separation, $A^3$ is preferably an ester bond or amide bond, more preferably an ester bond. $X^-$ is a halide ion, hydroxide ion, or acetate ion. From the viewpoint of reducing the cooling time necessary for cell separation, $X^-$ is preferably a halide ion or hydroxide ion.

Examples of repeating units represented by Formula (9) of the present invention include repeating units generated by polymerizing trimethyl-2-methacryloyloxyethyl ammonium chloride, trimethyl-2-methacroyloxyethyl ammonium bromide, trimethyl-3-methacryloxypropyl ammonium chloride, or trimethyl-3-methacroyloxyethyl ammonium bromide as a monomer, repeating units generated by reacting repeating units generated by polymerizing 2-dimethylaminoethyl (meth)acrylate, 2-diethylaminoethyl (meth)acrylate, 3-dimethylaminopropyl (meth)acrylate, 3-diethylaminopropyl (meth)acrylate, dimethyl [(meth)acrylamidoethyl] amine, diethyl [(meth)acrylamidoethyl] amine, dimethyl [3-(meth)acrylamidopropyl] amine, or diethyl [3-(meth)acrylamidopropyl] amine as a monomer, with a $C_{1-4}$ halogenated alkyl, ethylene oxide, propylene oxide, 1,2-butylene oxide, or 2-chloroethyl methyl ether. Among these repeating units, repeating units generated by reacting repeating units generated by polymerizing 2-dimethylaminoethyl (meth)acrylate, 3-dimethylaminopropyl (meth)acrylate, dimethyl [(meth) acrylamidoethyl] amine, or dimethyl [3-(meth)acrylamidopropyl] amine as a monomer, with a $C_{1-4}$ halogenated alkyl, ethylene oxide, propylene oxide, 1,2-butylene oxide, or 2-chloroethyl methyl ether are preferable.

From the viewpoints of controlling cell adhesiveness and reducing the cooling time necessary for cell separation, among repeating units represented by the above Formulae (4) to (9), as block (B) constituting the block copolymer of the present invention, repeating units represented by Formula (4), Formula (5), Formula (6), or Formula (8) are preferable, and from the viewpoint of promoting cell adhesiveness, repeating units represented by Formula (5) or Formula (8) are more preferable.

Block (C) of the present invention is a hydrophobic polymer block which does not have an LCST in the range of 0° C. to 50° C. and which has an HLB value in the range of 0 to less than 9. Block (C) is a block contributing to the adhesion of the block copolymer of the present invention to a substrate. Note that HLB value used in the present description is defined above.

When the HLB value of block (C) of the present invention is equal to or greater than 9, a membrane applied to a substrate is likely to separate in water and a stable membrane cannot be obtained. Thus, the HLB value of block (C) of the present invention must be in the range of 0 to less than 9, and is preferably in the range of 0 to 8, more preferably in the range of 0 to 7.

As long as the HLB value is in the range of 0 to less than 9, block (C) of the present invention may include a monomer comprising the aforementioned hydrophilic moiety. Examples thereof include a copolymer of a monomer including the aforementioned hydrophilic moiety and an alkyl (meth)acrylate or a styrene derivative.

Block (C) constituting the block copolymer of the present invention is not particularly limited as long as it is a polymer block having an HLB value in the range of 0 to less than 9. Preferred examples of the repeating units constituting block (C) are the repeating units represented by Formulae (10) and (11) below. Block (C) may be composed of a single type of repeating unit or may be composed of two or more types of repeating units.

In the formula, $R^{33}$ is a hydrogen atom or methyl group. Y is a hydrogen atom, chlorine atom, acetoxy group, nitrile group, or $C_{6-30}$ aromatic hydrocarbon group. From the viewpoint of obtaining a stable membrane which does not separate in water, a hydrogen atom, chlorine atom, or $C_{6-30}$ aromatic hydrocarbon group is preferably used. Examples of $C_{6-30}$ aromatic hydrocarbon groups include phenyl groups, 1-naphthaline groups, 2-naphthaline groups, 9-anthracene groups, 1-pyrene groups and derivatives thereof.

Examples of repeating units represented by Formula (10) of the present invention include repeating units generated by polymerizing monomers selected from ethylene, vinyl chloride, vinyl acetate, acrylonitrile, styrene, 1-vinylnaphthalene, 2-vinylnaphthalene, 9-vinylanthracene, and 1-vinylpyrene. Among these, from the viewpoint of adhesion when applied to a substrate, repeating units generated by polymerizing styrene, 1-vinylnaphthalene, 2-vinylnaphthalene, 9-vinylanthracene, or 1-vinylpyrene are preferred, and repeating units generated by polymerizing styrene are more preferred.

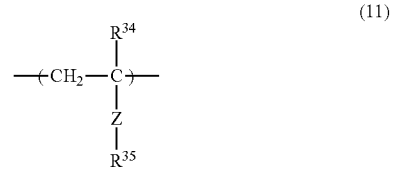

In the Formula, $R^{34}$ is a hydrogen atom or methyl group. $R^{35}$ is a $C_{1-30}$ hydrocarbon group. Examples thereof include methyl groups, ethyl groups, n-propyl groups, isopropyl groups, cyclopropyl groups, n-butyl groups, isobutyl groups, tert-butyl groups, n-hexyl groups, isohexyl groups, n-octyl groups, n-decyl groups, n-dodecyl groups, n-hexadecyl groups, and n-octadecyl groups. From the viewpoint of obtaining a stable membrane which does not separate in water, an n-butyl group, isobutyl group, tert-butyl group, n-hexyl group, isohexyl group, n-octyl group, n-decyl group, n-dodecyl group, n-hexadecyl group, or n-octadecyl group is preferably used.

Z is a divalent bond selected from the group consisting of an ester bond, amide bond, urethane bond, and ether bond. From the viewpoint of obtaining a stable membrane which does not separate in water, an ester bond or amide bond is preferable, and an ester bond is more preferable.

Examples of repeating units represented by Formula (11) of the present invention include repeating units generated by polymerizing a monomer selected from (meth)acrylate compounds such as methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth) acrylate, n-pentyl (meth)acrylate, n-hexyl (meth)acrylate, n-octyl (meth)acrylate, n-decyl (meth)acrylate, n-undecyl (meth)acrylate, n-dodecyl (meth)acrylate, n-tetradecyl (meth)acrylate, n-hexadecyl (meth)acrylate, n-octadecyl (meth)acrylate, and n-eicosyl (meth)acrylate, (meth)acrylamide compounds such as N-n-octyl (meth)acrylamide, N-n-decyl (meth)acrylamide, N-n-dodecyl (meth)acrylamide, N-n-hexadecyl (meth)acrylamide, and N-n-octadecyl (meth)acrylamide; and N-vinyl amide compounds such as N-vinyl-n-octylamide, N-vinyl-n-decylamide, N-vinyl-n-dodecylamide, and N-vinyl-n-hexadecylamide. Among these, from the viewpoint of obtaining a stable membrane which does not separate in water, repeating units generated by polymerizing an acrylate compound such as ethyl (meth)acrylate, n-propyl (meth)acrylate, n-butyl (meth)acrylate, n-pentyl (meth)acrylate, n-hexyl (meth)acrylate, n-heptyl (meth)acrylate, n-octyl (meth)acrylate, and n-tridecyl (meth)acrylate are preferable.

Further, in addition to the above, examples of block (C) of the present invention include polymers comprising at least one selected from N-alkyl maleimide compounds such as N-cyclohexyl maleimide and N-phenyl maleimide; fumaric acid diester compounds such as di-tert-butyl fumarate and di-n-butyl fumarate; N-vinylimidazole, and N-vinylcarbazole.

Block (A), block (B), and block (C) constituting the block copolymer of the present invention may be directly bonded or may be bonded via a small molecule spacer. The number of atoms of the spacer is not particularly limited as long as the effect of the present invention described above is not impaired thereby, and is preferably 2 atoms to 30 atoms. Furthermore, the structure of the spacer is not particularly limited as long as the effect of the present invention is not impaired thereby, and may be linear, branched or cyclic. For example, at least one of the bonds between the blocks may be a divalent bond containing at least one bond among the divalent bonds represented by the following Formulae (12) and (13).

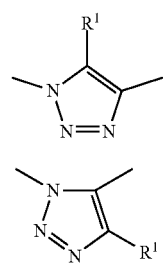

In the Formulae, $R^1$ is a hydrogen atom or $C_{1-20}$ hydrocarbon group. Examples of $C_{1-20}$ hydrocarbon groups include methyl groups, ethyl groups, n-propyl groups, isopropyl groups, n-butyl groups, isobutyl groups, n-hexyl groups, and n-octyl groups. From the viewpoint of stabilizing the bond between each block, $R^1$ is preferably a hydrogen atom.

The order of arrangement of block (A), block (B), and block (C) constituting the block copolymer of the present invention is not particularly limited, and can be, for example, (A)-(B)-(C), (A)-(C)-(B), or (B)-(C)-(A). Furthermore, the block copolymer of the present invention may include each block (A), (B) and (C) twice or more and the blocks may be randomly arranged. For example, (A)-(B)-(A)-(C), (A)-(B)-(C)-(A), etc., are also acceptable.

Furthermore, the block copolymer of the present invention may include another polymer block (X) other than block (A), block (B), and block (C) constituting the block copolymer. Examples of the specific arrangement in such a case include (A)-(B)-(C)-(X), (A)-(B)-(X)-(C), (A)-(C)-(B)-(X), (A)-(C)-(X)-(B), (A)-(X)-(B)-(C), (A)-(X)-(C)-(B), (B)-(A)-(C)-(X), (B)-(A)-(X)-(C), (B)-(C)-(A)-(X), (B)-(X)-(A)-(C), (C)-(A)-(B)-(X), and (C)-(B)-(A)-(X). Polymer block (X) may be any of block (A), block (B), and block (C) of the present invention as long as the aforementioned effect of the present invention is not impaired thereby, and may be, in addition to these blocks, for example, a temperature-reactive block having an LCST exceeding 50° C., a hydrophilic polymer block which has an LCST in the range of 0° C. to 50° C. and which has an HLB value (as determined by the Griffin method) in the range of 9 to 20, or a hydrophobic polymer block which has an LCST in the range of 0° C. to 50° C. and which has an HLB value (as determined by the Griffin method) in the range of 0 to less than 9. Among these sequences, from the viewpoint of reducing the cooling time necessary for cell separation, a sequence in which block (A), which is a temperature-responsive polymer block, and block (B), which is a hydrophilic polymer block, are not consecutive, i.e., (A)-(C)-(B), (A)-(C)-(B)-(X), (A)-(C)-(X)-(B), (A)-(X)-(B)-(C), (A)-(X)-(C)-(B), (B)-(C)-(A)-(X), or (B)-(X)-(A)-(C), is preferable, and (A)-(C)-(B), (A)-(C)-(B)-(X), or (B)-(C)-(A)-(X) is more preferable. In the present description, the term "partial copolymer" means a copolymer lacking any one of the essential blocks (A), (B) and (C). Examples thereof include (A)-(B), (A)-(C), (A)-(B)-(X), (A)-(X)-(C), etc.

The ratio of block (A) to the total amount of block (A), block (B), and block (C) constituting the block copolymer of the present invention is not particularly limited as long as it is 1 to 90 mol %. From the viewpoints imparting cell adhesion to the cell culture substrate coated with a substrate including a surface treatment agent comprising the block copolymer of the present invention and reducing the cooling time necessary for cell separation, 25 to 85 mol % is preferable and 45 to 65 mol % is more preferable. When the ratio of block (A) to all repeating units is less than 1 mol %, cell adhesiveness decreases, and when it exceeds 90 mol %, the cooling time necessary for cell separation increases.

The ratio of block (B) to the total amount of block (A), block (B), and block (C) constituting the block copolymer of the present invention is not particularly limited as long as it is 1 to 90 mol %. From the viewpoints imparting cell adhesion to the cell culture substrate coated with a substrate including a surface treatment agent comprising the block copolymer of the present invention and reducing the cooling time necessary for cell separation, 2 to 50 mol % is preferable and 5 to 30 mol % is more preferable. When the ratio of block (B) to all repeating units is less than 1 mol %, the cooling time necessary for cell separation increases, and when it exceeds 90 mol %, cell adhesiveness decreases.

The ratio of block (C) to the total amount of block (A), block (B), and block (C) constituting the block copolymer of the present invention is not particularly limited as long as it is 1 to 90 mol %. From the viewpoints imparting cell adhesion to the cell culture substrate and reducing the cooling time necessary for cell separation when coating a substrate with a surface treatment agent comprising the block copolymer of the present invention, 10 to 70 mol % is preferable and 20 to 50 mol % is more preferable. When the ratio of block (C) to all repeating units is less than 1 mol %, cell adhesiveness decreases, and during cooling, the block copolymer elutes into the medium. When it exceeds 90 mol %, the cooling time necessary for cell separation increases.

The ratio of block (A), block (B), and block (C) constituting the block copolymer of the present invention is not particularly limited as long it is within the range of the ratio of each block to all the repeating units described above. From the viewpoints of imparting cell adhesion to the cell culture substrate described above and reducing the cooling time necessary for cell improvement, the ratio of block (A) to block (B) is preferably in the range of 0.5:1 to 50:1, more preferably in the range of 1.5:1 to 15:1. Furthermore, from the viewpoints of imparting adhesion to the substrate of the block copolymer of the present invention and shortening the cooling time necessary for cell separation, the ratio of block (A) to block (C) is preferably in the range of 0.25:1 to 10:1, more preferably in the range of 0.5:1 to 5:1. Further, from the viewpoints of imparting cell adhesion to the aforementioned cell culture substrate, imparting adhesion to the substrate of the block copolymer of the present invention, and reducing the cooling time necessary for cell separation, the ratio of block (B) to block (C) is preferably in the range of 0.01:1 to 5:1, more preferably in the range of 0.1:1 to 2:1.

The number average molecular weight (Mn) of the block copolymer of the present invention is in the range of 3,000 to 1,000,000, preferably 4,000 to 500,000, more preferably 5,000 to 200,000. When the number average molecular weight is less than 3,000, even when applied to a cell culture substrate, the block copolymer will elute from the substrate into the culture medium in the cell culture. Furthermore, when the number average molecular weight exceeds 1,000,000, solution viscosity increases, making it difficult to apply to the cell culture substrate.

The block copolymer of the present invention can be produced by a method comprising the following steps (1) to (3).

(1) Producing any one of the blocks from among block (A), block (B), and block (C) of the present invention, (2) producing a partial block copolymer comprising the block produced in step (1) and, connected thereto, one of the blocks from among blocks (A), (B), and (C) in the present invention except the block produced in step (1); and (3) producing a block copolymer comprising the partial block copolymer produced in step (2) and, connected thereto, the block among blocks (A), (B), and (C) in the present invention which does not constitute a block copolymer comprising the partial block copolymer produced in step (2).

From the viewpoint of carrying out block copolymerization with different types of monomers, each block constituting the block copolymer of the present invention is preferably produced by living polymerization such as living cationic polymerization, living anionic polymerization, or living radical polymerization. Among these types of living polymerization, from the viewpoint of ease of controlling the polymerization reaction, living radical polymerization is preferably used. For example, each block constituting the block copolymer of the present invention is more preferably produced using the living radical polymerization technology described in the "Radical Jugo Handbook" (Radical Polymerization Handbook), pp. 161-225 (2010), published by NTS Inc., Japan. Examples of living radical polymerization include atom transfer radical polymerization (ATRP), reversible addition fragmentation chain transfer polymerization (RAFT), and nitroxide-mediated polymerization (NMP). Among these, from the viewpoint of a lack of necessity of the use of metals exhibiting toxicity, each block constituting the block copolymer of the present invention is preferably produced using RAFT polymerization.

Examples of specific methods for producing the block copolymer of the present invention include a method (A-B-C) in which the monomer for generating block A is polymerized, thereafter, the monomer for generating block (B) is polymerized, and subsequently, the monomer for generating block (C) is polymerized; a method (A-C-B) in which the monomer for generating block (A) is polymerized, thereafter, the monomer for generating block (C) is polymerized, and subsequently, the monomer for generating block (B) is polymerized; a method (B-A-C) in which the monomer for generating block (B) is polymerized, thereafter, the monomer for generating block (A) is polymerized, and subsequently, the monomer for generating block (C) is polymerized; a method (B-C-A) in which the monomer for generating block (B) is polymerized, thereafter, the monomer for generating block (C) is polymerized, and subsequently, the polymer for generating block (A) is polymerized; a method (C-A-B) in which the monomer for generating block (C) is polymerized, thereafter, the monomer for generating block (A) is polymerized, and subsequently, the polymer for generating block (B) is polymerized; and a method (C-B-A) in which the monomer for generating block (C) is polymerized, thereafter, the monomer for generating block (B) is polymerized, and subsequently, the monomer for generating block (A) is polymerized.

Furthermore, as described above, the block copolymer of the present invention may include another block (X) in addition to block (A), block (B), and block (C) constituting the block copolymer of the present invention. Examples of specific production methods in such a case include a method (A-B-C-X) in which the monomer for generating block (A) is polymerized, then the monomer for generating block (B) is polymerized, thereafter, the monomer for generating block (C) is polymerized, and subsequently the monomer for generating block (X) is polymerized; a method (A-B-X-C) in which the monomer for generating block (A) is polymerized, then the monomer for generating block (B) is polymerized, thereafter, the monomer for generating block (X) is polymerized, and subsequently the monomer for generating block (C) is polymerized; a method (A-C-B-X) in which the monomer for generating block (A) is polymerized, then the monomer for generating block (C) is polymerized, thereafter, the monomer for generating block (B) is polymerized, and subsequently the monomer for generating block (X) is polymerized: a method (A-C-X-B) in which the monomer for generating block (A) is polymerized, then the monomer for generating block (C) is polymerized, thereafter, the monomer for generating block (X) is polymerized, and subsequently the monomer for generating block (B) is polymerized; a method (A-X-B-C) in which the monomer for generating block (A) is polymerized, then the monomer for generating block (X) is polymerized, thereafter, the monomer for generating block (B) is polymerized, and subsequently the monomer for generating block (C) is polymerized; a method (A-X-C-B) in which the monomer for generating block (A) is polymerized, then, the monomer for generating block (X) is polymerized, thereafter, the monomer for generating block (C) is polymerized, and subsequently the monomer for generating block (B) is polymerized: a method (B-A-C-X) in which the monomer for generating block (B) is polymerized, then the monomer for generating block (A) is polymerized, thereafter, the monomer for generating block (C) is polymerized, and subsequently the monomer for generating block (X) is polymerized: a method (B-A-X-C) in which the monomer for generating block (B) is polymerized, then the monomer for generating block (A) is polymerized, thereafter, the monomer for generating block (X) is polymerized, and subsequently the monomer for generating block (C) is polymerized; a method (B-C-A-X) in which the monomer for generating block (B) is polymerized, then the monomer for generating block (C) is polymerized, thereafter, the monomer for generating block (A) is polymerized, and subsequently the monomer for generating block (X) is polymerized: a method (B-C-X-A) in which the monomer for generating block (B) is polymerized, then the monomer for generating block (C) is polymerized, thereafter, the monomer for generating block (X) is polymerized, and subsequently the monomer for generating block (A) is polymerized; a method (B-X-A-C) in which the monomer for generating block (B) is polymerized, then the monomer for generating block (X) is polymerized, thereafter, the monomer for generating block (A) is polymerized, and subsequently the monomer for generating block (C) is polymerized; a method (B-X-C-A) in which the monomer for generating block (B) is polymerized, then the monomer for generating block (X) is polymerized, thereafter, the monomer for generating block (C) is polymerized, and subsequently the monomer for generating block (A) is polymerized: a method (C-A-B-X) in which the monomer for generating block (C) is polymerized, then the monomer for generating block (A) is polymerized, thereafter, the monomer for generating block (B) is polymerized, and subsequently the monomer for generating block (X) is polymerized; a method (C-A-X-B) in which the monomer for generating block (C) is polymerized, then the monomer for generating block (A) is polymerized, thereafter, the monomer for generating block (X) is polymerized, and subsequently the monomer for generating block (B) is polymerized; a method (C-B-A-X) in which the monomer for generating block (C) is polymerized, then the monomer for generating block (B) is polymerized, thereafter, the monomer for generating block (A) is polymerized, and subsequently the monomer for generating block (X) is polymerized;
a method (C-B-X-A) in which the monomer for generating block (C) is polymerized, then the monomer for generating block (B) is polymerized, thereafter, the monomer for generating block (X) is polymerized, and subsequently the monomer for generating block (A) is polymerized; a method (C-X-A-B) in which the monomer for generating block (C) is polymerized, then the monomer for generating block (X) is polymerized, thereafter, the monomer for generating block (A) is polymerized, and subsequently the monomer for generating block (B) is polymerized; a method (C-X-B-A) in which the monomer for generating block (C) is polymerized, then the monomer for generating block (X) is polymerized, thereafter, the monomer for generating block (B) is polymerized, and subsequently the monomer for generating block (A) is polymerized; a method (X-A-B-C) in which the monomer for generating block (X) is polymerized, then the monomer for generating block (A) is polymerized, thereafter, the monomer for generating block (B) is polymerized, and subsequently the monomer for generating block (C) is polymerized; a method (X-A-C-B) in which the monomer for generating block (X) is polymerized, then the monomer for generating block (A) is polymerized, thereafter, the monomer for generating block (C) is polymerized, and subsequently the monomer for generating block (B) is polymerized; a method (X-B-A-C) in which the monomer for generating block (X) is polymerized, then the monomer for generating block (B) is polymerized, thereafter, the monomer for generating block (A) is polymerized, and subsequently the monomer for generating block (C) is polymerized; a method (X-B-C-A) in which the monomer for generating block (X) is polymerized, then the monomer for generating block (B) is polymerized, thereafter, the monomer for generating block (C) is polymerized, and subsequently the monomer for generating block (A) is polymerized: a method (X-C-A-B) in which the monomer for generating block (X) is polymerized, then the monomer for generating block (C) is polymerized, thereafter, the monomer for generating block (A) is polymerized, and subsequently the monomer for generating block (B) is polymerized; and a method (X-C-B-A) in which the monomer for generating block (X) is polymerized, then the monomer for generating block (C) is polymerized, thereafter, the monomer for generating block (B) is polymerized, and subsequently the monomer for generating block (A) is polymerized.

In the production of each of the blocks in the intermediate stage of the production of the block copolymer of the present invention, in the stage in which polymerization of the monomers for generating each of the blocks has ended, a portion of the reaction solution is sampled, the residual amount of unreacted monomer is measured by $^1$H-NMR or the like, and depending on the residual amount of unreacted monomers, each generated block may be purified or may be used for polymerization of a monomer that produces the next block without purification. For example, in the case in which there is a large residual amount of unreacted monomer after the polymerization for generating each block in the intermediate stage has completed and it is therefore considered that unreacted monomer will adversely affect the polymerization for producing the next block, it is preferable to purify the block produced by the polymerization by a known polymer purification method, such as solvent extraction, reprecipitation, recrystallization or the like. Specifically, when the residual amount of the unreacted monomer is 20% or more of the charged amount of the monomer, it is preferable to purify the block generated by the polymerization by the above-described method.

Conversely, in the case in which there is an insignificant residual amount of unreacted monomer after the polymerization for generating each block in the intermediate stage has completed and it is therefore not considered that unreacted monomer will adversely affect the polymerization for producing the next block, the block produced by the polymerization may not be purified and may be used for the polymerization of the monomer for generating the next block. Specifically, when the residual amount of the unreacted monomer is less than 20%, preferably less than 15%, the block produced by the polymerization may not be purified and may be used for the polymerization of the monomer for generating the next block.

In order to remove residual unreacted monomers at the stage of production of the target block copolymer of the present invention, it is preferable to purify the block copolymer of the present invention by a known polymer purification method such as solvent extraction, reprecipitation, recrystallization, or the like.

Further, a click chemistry reaction, as described in, for example, A. Michael, J. Prakt, Chem. 48, 94 (1893), R. Huisgen, in 1,3-Dipolar Cycloaddition Chemistry, ed. by A. Padwa. Wiley, New York. Vol. 1, pp. 1-176 (1984), C. W. Tomoe, C. Christensen, M. Meldal, J. Org. Chem. 67, pp. 3057-3062, and V. V. Rostovestev, L. G. Green, V. V. Fokin, K. B. Sharpless, Angew. Chem., Int. Ed. 41, pp. 2596-2599 (2002), can be used as the method for producing the block copolymer of the present invention.

Examples of specific methods for producing the block copolymer of the present invention using a click chemistry reaction include, in the case in which the block copolymer is produced using the aforementioned RAFT polymerization, a method ((A–B)+C) in which block (B) having an alkynyl group (or an azide group) at its terminal is synthesized by polymerizing the monomer for generating block (B), then the monomer for generating block (A) is polymerized, thereafter, a partial block body having an alkynyl group (or an azide group) at its terminal on the block (B) side is synthesized, and subsequently, block (C) having an azide group (or an alkynyl group) at its terminal is reacted; a method (A+(B–C)) in which block (B) having an alkynyl group (or an azide group) at its terminal is synthesized by polymerizing the monomer for generating block (B), then the monomer for generating block (C) is polymerized, thereafter, a partial block body having an alkynyl group (or an azide group) at its terminal on the block (B) side is synthesized, and subsequently, block (A) having an azide group (or an alkynyl group) at its terminal is reacted; a method ((A–C)+B) in which block (C) having an alkynyl group (or an azide group) at its terminal is synthesized by polymerizing the monomer for generating block (C), then the monomer for generating block (A) is polymerized, thereafter, a partial block body having an alkynyl group (or an azide group) at its terminal on the block (C) side is synthesized, and subsequently, block (B) having an azide group (or an alkynyl group) at its terminal is reacted; a method (A+(C–B)) in which block (C) having an alkynyl group (or an azide group) at its terminal is synthesized by polymerizing the monomer for generating block (C), then the monomer for generating block (B) is polymerized, thereafter, a partial block body having an alkynyl group (or an azide group) at its terminal on the block (C) side is synthesized, and subsequently, block (A) having an azide group (or an alkynyl group) at its terminal is reacted; a method ((B–A)+C) in which block (A) having an alkynyl group (or an azide group) at its terminal is synthesized by polymerizing the monomer for generating block (A), then the monomer for generating block (B) is polymerized, thereafter, a partial block body having an alkynyl group (or an azide group) at its terminal on the block (S) side is synthesized, and subsequently, block (C) having an azide group (or an alkynyl group) at its terminal is reacted; a method (B+(A–C)) in which block (A) having an alkynyl group (or an azide group) at its terminal is synthesized by polymerizing the monomer for generating block (A), then the monomer for generating block (C) is polymerized, thereafter, a partial block body having an alkynyl group (or an azide group) at its terminal on the block (A) side is synthesized, and subsequently, block (B) having an azide group (or an alkynyl group) at its terminal is reacted; a method ((B–C)+A) in which block (C) having an alkynyl group (or an azide group) at its terminal is synthesized by polymerizing the monomer for generating block (C), then the monomer for generating block (B) is polymerized, thereafter, a partial block body having an alkynyl group (or an azide group) at its terminal on the block (C) side is synthesized, and subsequently, block (A) having an azide group (or an alkynyl group) at its terminal is reacted; a method (B+(C–A)) in which block (C) having an alkynyl group (or an azide group) at its terminal is synthesized by polymerizing the monomer for generating block (C), then the monomer for generating block (A) is polymerized, thereafter, a partial block body having an alkynyl group (or an azide group) at its terminal on the block (C) side is synthesized, and subsequently, block (B) having an azide group (or an alkynyl group) at its terminal is reacted; a method ((C–A)+B) in which block (A) having an alkynyl group (or an azide group) at its terminal is synthesized by polymerizing the monomer for generating block (A), then the monomer for generating block (C) is polymerized, thereafter, a partial block body having an alkynyl group (or an azide group) at its terminal on the block (A) side is synthesized, and subsequently, block (B) having an azide group (or an alkynyl group) at its terminal is reacted; a method (C+(A–B)) in which block (A) having an alkynyl group (or an azide group) at its terminal is synthesized by polymerizing the monomer for generating block (A), then the monomer for generating block (B) is polymerized, thereafter, a partial block body having an alkynyl group (or an azide group) at its terminal on the block (A) side is synthesized, and subsequently, block (C) having an azide group (or an alkynyl group) at its terminal is reacted; a method ((C–B)+A) in which block (B) having an alkynyl group (or an azide group) at its terminal is synthesized by polymerizing the monomer for generating block (B), then the monomer for generating block (C) is polymerized, thereafter, a partial block body having an alkynyl group (or an azide group) at its terminal on the block (B) side is synthesized, and subsequently, block (A) having an azide group (or an alkynyl group) at its terminal is reacted; and a method (C+(B–A)) in which block (B) having an alkynyl group (or an azide group) at its terminal is synthesized by polymerizing the monomer for generating block (B), then the monomer for generating block (A) is polymerized, thereafter, a partial block body having an alkynyl group (or an azide group) at its terminal on the block (B) side is synthesized, and subsequently, block (C) having an azide group (or an alkynyl group) at its terminal is reacted.

In the production of the block copolymer of the present invention using the aforementioned click chemistry reaction, the block copolymer of the present invention is produced by a click chemistry reaction using the blocks generated by the polymerization of monomers, and thus, from the viewpoint of suppressing side reactions during the click chemistry reaction, it is preferable to purify each generated block after the polymerization of the monomers for generating each block is completed.

Furthermore, when the block copolymer of the present invention is produced using the aforementioned click chemistry reaction, a divalent bond as shown in the Formula (1) or (2) is introduced into at least one of the blocks in the block copolymer of the present invention.

2. Surface Treatment Agent

The surface treatment agent for substrates of the present invention includes the block copolymer of the present invention. The application of the surface treatment agent of the present invention is not particularly limited. The surface treatment agent of the present invention is preferably used for cell culture substrates such as petri dishes, multi-well plates, flasks, and microcarriers.

The surface treatment agent of the present invention can perform surface treatment by merely being applied to a substrate. The surface treatment agent of the present invention may include, in addition to the block copolymer of the present invention, a solvent which can dissolve the block copolymer of the present invention. The solvent which can dissolve the block copolymer of the present invention is not particularly limited. From the viewpoints of preventing the dissolution of the substrate when applied to the substrate and evaporating so as not remain on the substrate after coating, the solvent is preferably water or a $C_{1-3}$ alcohol-type solvent. Ethanol or a mixed solvent of water and ethanol is particularly preferable from the viewpoint of the insignificant influence thereof on the cultured cells when the solvent remains on the substrate. Though the surface treatment agent of the present invention is generally in the form of a solution, it may be in a powder form dissolvable in the aforementioned solvent.

The target substrate of the surface treatment agent of the present invention is not particularly limited. Since the block copolymer adheres to the substrate by hydrophobic interaction, various hydrophobic polymer materials are preferably used. Examples of hydrophobic polymer materials include acrylic polymers such as polymethyl methacrylate, and various silicone rubbers such as polydimethylsiloxane, polystyrene, polyethylene terephthalate, and polycarbonate. Furthermore, metal substrates, ceramic substrates, or glass substrates which have been subjected to surface treatment with a silane coupling agent can also be used.

Furthermore, the form of the substrate is not particularly limited and can be, for example, plate-like, bead-like, and fiber-like shapes, and additionally holes, grooves, or protrusions may be provided on the substrate. Examples of the method for applying the surface treatment agent of the present invention to a substrate include various commonly known methods such as brush coating, dip coating, spin coating, bar coating, flow coating, spray coating, roll coating, air-knife coating, and blade coating.

3. Membrane

The membrane of the present invention is a membrane obtained by applying the surface treatment agent of the present invention onto various substrates and drying. By including block (C) in the block copolymer of the present invention, the block copolymer has adhesiveness to the cell culture substrate, and by including block (A) in the block copolymer of the present invention, at 37° C. or higher, which is the cell culture temperature, the membrane surface exhibits hydrophobicity, thereby enabling the adhesion of proteins and enabling the adhesion of cells to the culture. Further, after cell culturing, by reducing the temperature, the membrane surface becomes hydrophilic, thereby promoting cell separation. By including block (B) in the block copolymer of the present invention, it is possible to reduce the cooling time required for separation.

The thickness of the membrane of the present invention is 1 nm to 10 µm, preferably 10 nm to 5 µm, more preferably 30 nm to 500 nm, particularly preferably 50 nm to 200 nm. When the thickness of the membrane is less than 1 nm, when applied to a cell culture substrate, the cooling time necessary for cell separation becomes long. When the thickness of the membrane exceeds 10 µm, when applied to a cell culture substrate, cell adhesion decreases.

4. Substrate for Cell Culture and Cell Culture Method Using the Cell Culture Substrate The substrate for cell culture of the present invention is a substrate for cell culture in which the substrate surface is coated with the membrane of the present invention. The cell culture using the cell culture substrate of the present invention is performed at a temperature higher than the LCST of the block copolymer applied to the surface of the culture substrate. When human-derived cells are used, in order to obtain high culture efficiency, it is preferable to perform cell culture at a temperature around human body temperature, more preferably in the temperature range of 35 to 39° C., and particularly preferably in the temperature range of 36 to 38° C. The other culture conditions are not particularly limited and culture may be carried out under conditions normally performed in the art. For example, as the medium, a serum such as fetal bovine serum may be added, or a serum-free medium may be used.

After culture, to detach the proliferated cells from the cell culture substrate, it is only necessary to change the ambient temperature to a temperature lower than the LCST of block (A) constituting the block copolymer of the present invention, preferably 10° C. lower than the LCST. The separation of the cells from the cell culture substrate by cooling to below the LCST can be carried out in the culture medium in which the cells were cultured or in another medium or a phosphate buffer solution, and can be selected in accordance with purpose. At that time, in order to effectively and easily detach the proliferated cells, the cell culture substrate may be tapped lightly, shaken, or the medium may be stirred using a pipette or the like.

When the cell culture substrate of the present invention is used, preferably cultured cells having a maximum diameter of 5 µm to 300 µm can be detached merely by cooling, and more preferably cells in the form of a single cell can be detached by merely cooling. The size and shape of the detached cells can be adjusted by selecting the composition and molecular weight of the block copolymer, the structure of the cell culture substrate, method for producing the cell culture substrate, the cell culture method, and the type of cultured cells. For example, by increasing the ratio of block (B) in the block copolymer, increasing the thickness of the block copolymer in the cell culture substrate production method, and increasing the roughness of the culture substrate surface, the size of the cell cluster can be reduced, whereby single cells can be detached.

The cells which can be cultured using the cell culture substrate of the present invention are not particularly limited as long as they can adhere to the surface of the cell culture substrate prior to stimulation by temperature reduction. Examples thereof include human bone marrow-derived mesenchymal stem cells, human adipose tissue-derived mesenchymal stem cells, human lung-derived fibroblasts, human skin fibroblasts, CHO cells derived from Chinese hamster ovary, murine connective tissue L929 cells, human embryonic kidney-derived cells HEK 293 cells, human cervical carcinoma-derived HeLa cells and the like, as well as various tissues in the living body, such as epithelial cells and endothelial cells constituting organs, skeletal muscle cells showing contractility, smooth muscle cells, neuronal cells constituting the nervous system, glial cells, fibroblast cells, hepatocytes involved in the metabolism of the living body, liver non-parenchymal cells and adipocytes, stem cells existing in various tissues, and cells differentiated therefrom. Examples other than these include cells (living cells) contained in blood, lymph fluid, cerebrospinal fluid, sputum, urine or feces, microorganisms existing in the body or the environment, viruses, protozoa and the like.

EXAMPLES

The Examples of the present invention will be described below. However, these Examples do not limit the present invention in any way. Unless otherwise noted, commercially available reagents were used.

<Composition of Block Copolymer>

The composition of the block copolymer was determined by proton nuclear magnetic resonance ($^1$H-NMR) spectral analysis using a nuclear magnetic resonance measurement device (manufactured by JEOL Ltd.; product name: JNM-ECZ 400S/L1).

<Molecular Weight and Molecular Weight Distribution of Block Copolymer>

The weight average molecular weight (Mw), number average molecular weight (Mn), and molecular weight distribution (Mw/Mn) were measured by gel permeation chromatography (GPC). An HLC-8320 GPC manufactured by Tosoh Corporation was used as the GPC device, two TSKgel Super AWM-H manufactured by Tosoh Corporation were used as columns, the column temperature was set to 40° C., and 1,1,1,3,3,3-Hexafluoro-2-propanol containing 10 mM of sodium trifluoroacetate or N,N-dimethylformamide containing 10 mM of lithium bromide was used as the eluent. A 1.0 mg/mL measurement sample was prepared and measured. The molecular weight calibration curve was prepared with polymethylmethacrylate having a known molecular weight (manufactured by Polymer Laboratories Ltd.).

<Water Contact Angle of Substrate Surface>

The water contact angles (180−θ) (°) of the substrate surface at 40° C. and 20° C. were calculated by measuring the air bubble contact angle (θ) (°) in water at 40° C. and 20° C. A contact angle of 3 μL of bubbles in water was measured as θ using a contact angle meter DM 300 manufactured by Kyowa Interface Science Co., Ltd. It is deemed that the greater the difference in the water contact angle at 40° C. and 20° C., the higher the ability to detach cells as a result of temperature responsiveness, i.e., temperature change.

Example 1

[Production of Polymer Block (B)]

1.50 g (5.1 mmol) of 2-methacryloyloxyethyl phosphorylcholine, 25.3 mg (63 μmol) of 4-cyano-4-[(dodecylsulfonylthiocarbonyl) sulfonyl] pentanoic acid as a RAFT agent, and 1 mg (6 μmol) of azobis(isobutyronitrile) as an initiator were added to a test tube and dissolved in 10.2 mL of a 1:1 mixed solution of 1,4-dioxane/ethanol. After nitrogen bubbling was carried out for 30 minutes, the mixture was reacted for 18 hours at 65° C. After reaction, the reaction solution was poured into 200 mL of a 20:1 mixed solution of acetone:methanol, and a precipitated yellow solid was filtered and dried under reduced pressure for 1 day to obtain a 2-methacryloyloxyethyl phosphorylcholine polymer (polymer block (B)). The formula weight of the hydrophilic moieties of the repeating units of the 2-methacryloyloxyethyl phosphorylcholine polymer block (B) were a total of 5 carbon, 8 hydrogen, 1 nitrogen, 6 oxygen, and 1 phosphorus (209.1). The total formula weight of the repeating unit was 295.3 and the HLB value (as determined by the Griffin method) was 14.

[Partial Block Copolymer Production]

1.50 g of the above polymer block (B), 1.71 g (12.0 mmol) of n-butyl methacrylate, and 2 mg (13 μmol) of azobis(isobutyronitrile) were added to a test tube and dissolved in 12 mL of a 1:1 mixed solution of 1,4-dioxane/ethanol. After nitrogen bubbling was carried out for 30 minutes, the mixture was reacted for 24 hours at 65° C. After reaction, the reaction solution was poured into 300 ml of hexane, and a precipitated yellow solid was filtered and dried under reduced pressure for 1 day to obtain a partial block copolymer comprising the 2-methacryloyloxyethyl phosphorylcholine polymer block (B) and an n-butyl methacrylate polymer block (C). The formula weight of the hydrophilic moieties of the repeating units of the n-butyl methacrylate polymer block (C) are a total of 1 carbon and 2 oxygen (44.0). The total formula weight of the repeating unit is 142.2 and the HLB value was 6 (as determined by the Griffin method).

[Block Copolymer Production]

0.75 g of the above partial block copolymer, 0.93 g (8.2 mmol) of N-isopropylacrylamide, and 0.3 mg (2 μmol) of azobis(isobutyronitrile) were added to a test tube and dissolved in 8.2 mL of a 1:1 mixed solution of 1,4-dioxane/ethanol. After nitrogen bubbling was carried out for 30 minutes, the mixture was reacted for 24 hours at 65° C. After reaction, the reaction solution was poured into 200 mL of hexane, and a precipitated white solid was filtered and dried under reduced pressure for 1 day to obtain a block copolymer comprising the 2-methacryloyloxyethyl phosphorylcholine polymer block (B), the n-butyl methacrylate polymer block (C), and an N-isopropylacrylamide polymer block (A). The composition, Mn, and Mw/Mn of the obtained block copolymer are shown in Table 1.

[Surface Treatment Agent Preparation]

0.01 g of the above block copolymer was dissolved in 4.99 g of ethanol to produce a 0.2 wt % ethanol solution of the block copolymer. Further, 1 mL of the 0.2 wt % ethanol solution and 9 mL of ethanol were mixed to prepare a 0.02 wt % surface treatment agent.

[Membrane Evaluation]

0.2 mL of the obtained surface treatment agent was added to each well of a polystyrene 6-well plate for cell culture manufactured by Corning Co., and dried at room temperature. Thereafter, vacuum drying was performed for 6 hours to prepare a cell culture substrate having a membrane formed from the block copolymer comprising the 2-methacryloyloxyethyl phosphorylcholine polymer block (B), the n-butyl methacrylate polymer block (C), and the N-isopropylacrylamide polymer block (A) introduced onto the surface thereof. The membrane thickness was 50 nm. The water contact angles at 40° C. and 20° C. are shown in Table 1. The water contact angle at 20° C. was lower than the water contact angle at 40° C. and was less than 40°, indicating high hydrophilicity.

[Cell Culture Evaluation and Separation Evaluation]

Murine connective tissue L929 cells (100 cells/mm$^2$) were cultured at 37° C. and a $CO_2$ concentration of 5% using the cell culture substrate having a membrane formed from the block copolymer comprising the 2-methacryloyloloxyethyl phosphorylcholine polymer block (B), the n-butyl methacrylate polymer block (C), and the N-isopropylacrylamide polymer block (A) introduced onto the surface thereof produced as described above. Dulbecco-Forcot modified Eagle minimum essential medium containing 10 vol % fetal bovine serum (10 vol % FBS/DMEM) was used as the culture solution. Cell proliferation was confirmed and culturing was carried out until cultured cells covered 100% of the substrate. Thereafter, the number of cells was confirmed with a 10×10 magnification microscope. After cooling the substrate to 10° C. the detached cells were removed with an aspirator, and the number of cells was confirmed again with a 10×10 magnification microscope. By cooling for 15 minutes, 100% of the cells were detached.

Reference Example 1

[Surface Treatment Agent Preparation]

Preparation was performed in the same manner as in the section [Surface Treatment Agent Preparation] of Example 1 except that the partial block copolymer comprising the 2-methacryloyloxyethyl phosphorylcholine polymer block (B) and the n-butyl methacrylate polymer block (C) produced in the section [Partial Block Copolymer Production] of Example 1 was used in place of the block copolymer to prepare a 0.02 wt % surface treatment agent.

[Membrane Evaluation]

Preparation of a cell culture substrate was performed by the same method as the method described in the section [Membrane Evaluation] of Example 1 except that the above surface treatment agent was used to prepare a cell culture substrate having a membrane formed from the partial block copolymer comprising the 2-methacryloyloxyethyl phosphorylcholine polymer block (B) and the n-butyl methacrylate polymer block (C) introduced onto the surface thereof. The membrane thickness was 50 nm. The water contact angles at 40° C. and 20° C. were evaluated and were the same contact angle (15°), indicating high hydrophilicity and exhibiting no temperature responsiveness.

[Cell Culture Evaluation]

Cell culture evaluation was performed for 5 days in the same manner as in [Cell Culture Evaluation and Separation Evaluation] of Example 1 except that the cell culture substrate having a membrane formed from the partial block copolymer comprising the 2-methacryloyloxyethyl phosphorylcholine polymer block (B) and the n-butyl methacrylate polymer block (C) introduced onto the surface thereof prepared as described above was used. The cells did not adhere to the substrate and proliferation could not be confirmed.

Example 2

[Cell Culture Evaluation and Separation Evaluation]

Evaluation was performed in the same manner as in the section [Cell Culture Evaluation and Separation Evaluation] of Example 1 using the cell culture substrate having a membrane formed from the block copolymer comprising the 2-methacryloyloxyethyl phosphorylcholine polymer block (B), the n-butyl methacrylate polymer block (C), and the N-isopropylacrylamide polymer block (A) introduced onto the surface thereof prepared in the section [Membrane Evaluation] of Example 1 except that Chinese hamster ovary-derived CHO cells (100 cells/mm$^2$) were used in place of murine connective tissue L929 cells (100 cells/mm$^2$) and 10 vol % of FBS/Ham's F-12 was used as the culture solution in place of the 10 vol % FBS/DMEM, and cell proliferation was confirmed. Furthermore, after culturing until the cultured cells covered 100% of the substrate, by cooling the substrate to 10° C., 70% of the cells were detached after 15 minutes.

Reference Example 2

[Cell Culture Evaluation]

Cell culture evaluation was performed for 5 days in the same manner as in the section [Cell Culture Evaluation and Separation Evaluation] of Example 1 using the cell culture substrate having a membrane formed from the partial block copolymer comprising the 2-methacryloyloxyethyl phosphorylcholine polymer block (B) and the n-butyl methacrylate polymer block (C) introduced onto the surface thereof prepared in the section [Membrane Evaluation] of Reference Example 1 except that Chinese hamster ovary-derived CHO cells (100 cells/mm$^2$) were used in place of murine connective tissue L929 cells (100 cells/mm$^2$) and 10 vol % of FBS/Ham's F-12 was used as the culture solution in place of the 10 vol % FBS/DMEM. The cells did not adhere to the substrate and proliferation could not be confirmed.

Example 3

[Production of Polymer Block (B)]

Synthesis was performed by the same method as in the section [Production of Polymer Block (B)] of Example 1 except that 43 mg (106 μmol) of 4-cyano-4-[(dodecylsulfonylthiocarbonyl) sulfonyl] pentanoic acid and 1.7 mg (10 μmol) of azobis(isobutyronitrile) were used and reaction was carried out for 14 hours to obtain a 2-methacryloyloxyethyl phosphorylcholine polymer (polymer block (B)).

[Partial Block Copolymer Production]

Production was performed by the same method as in the section [Partial Block Copolymer Production] of Example 1 except that 1.0 g of the above polymer block (B), 2.40 g (16.9 mmol) of n-butyl methacrylate, 2.5 mg (15 μmol) of azobis(isobutyronitrile), and 17 mL of a 1:1 mixed solution of 1,4-dioxane/ethanol were used to obtain a partial block copolymer comprising the 2-methacryloyloxyethyl phosphorylcholine polymer block (B) and an n-butyl methacrylate polymer block (C).

[Block Copolymer Production]

Production was performed by the same method as in the section [Block Copolymer Production] of Example 1 except that 0.50 g of the above partial block polymer, 0.62 g (5.5 mmol) of N-isopropylacrylamide, 0.2 mg (1 μmol) of azobis (isobutyronitrile), and 5.5 mL of a 1:1 mixed solution of 1,4-dioxane/ethanol were used to obtain a block copolymer comprising the 2-methacryloyloxyethyl phosphorylcholine polymer block (B), the n-butyl methacrylate polymer block (C), and an N-isopropylacrylamide polymer block (A). The composition, Mn, and Mw/Mn of the obtained block copolymer are shown in Table 1.

[Surface Treatment Agent Preparation]

Preparation was performed by the same method as in the section [Surface Treatment Agent Preparation] of Example 1 except that the above block copolymer was used to prepare a surface treatment agent.

[Membrane Evaluation]

Preparation of a cell culture substrate was performed by the same method as the method described in the section [Membrane Evaluation] of Example 1, except that the above surface treatment agent was used, to prepare a cell culture substrate having a membrane formed from the block copolymer comprising the 2-methacryloyloxyethyl phosphorylcholine polymer block (B), the n-butyl methacrylate polymer block (C), and an N-isopropylacrylamide polymer block (A) introduced onto the surface thereof. The membrane thickness was 100 nm. The water contact angles at 40° C. and 20° C. are shown in Table 1. The water contact angle at 20° C. was lower than the water contact angle at 40° C. and was less than 40°, indicating high hydrophilicity.

[Cell Culture Evaluation and Separation Evaluation]

Evaluation was performed in the same manner as in the section [Cell Culture Evaluation and Separation Evaluation] of Example 1 except that the cell culture substrate having a membrane formed from the block copolymer comprising the 2-methacryloyloxyethyl phosphorylcholine polymer block (B), the n-butyl methacrylate polymer block (C), and an N-isopropylacrylamide polymer block (A) introduced onto the surface thereof prepared as described above was used, and cell proliferation was confirmed. Furthermore, after culturing until the cultured cells covered 100% of the substrate, by cooling the substrate to 10° C., 100% of the cells were detached after 15 minutes.

Reference Example 3

[Surface Treatment Agent Preparation]

Preparation was performed by the same method as in the section [Surface Treatment Agent Preparation] of Example 1, except that the partial block copolymer comprising the 2-methacryloyloxyethyl phosphorylcholine polymer block (B) and the n-butyl methacrylate polymer block (C) produced in the section [Partial Block Copolymer Production] of Example 3 was used in place of the block copolymer, to prepare a 0.02 wt % surface treatment agent.

[Membrane Evaluation]

Preparation of a cell culture substrate was performed by the same method as the method described in the section [Membrane Evaluation] of Example 1, except that the above surface treatment agent was used, to prepare a cell culture substrate having a membrane comprising the partial block copolymer comprising the 2-methacryloyloxyethyl phosphorylcholine polymer block (B) and the n-butyl methacrylate polymer block (C) introduced onto the surface thereof. The membrane thickness was 50 nm. The water contact angles at 40° C. and 20° C. were evaluated and were the same contact angle (23°), indicating high hydrophilicity and exhibiting no temperature responsiveness.

[Cell Culture Evaluation]

Cell culture evaluation was performed for 5 days in the same manner as in the section [Cell Culture Evaluation] of Example 1, except that the cell culture substrate having a membrane comprising the partial block copolymer comprising the 2-methacryloyloxyethyl phosphorylcholine polymer block (B) and the n-butyl methacrylate polymer block (C) introduced onto the surface thereof prepared as described above was used. The cells did not adhere to the substrate and proliferation could not be confirmed.

Example 4

[Cell Culture Evaluation and Separation Evaluation]

Evaluation was performed in the same manner as in the section [Cell Culture Evaluation and Separation Evaluation] of Example 1, except that the cell culture substrate having a temperature-responsive membrane introduced onto the surface thereof prepared in the section [Membrane Evaluation] of Example 3 was used, Chinese hamster ovary-derived CHO cells (100 cells/mm$^2$) were used in place of murine connective tissue L929 cells (100 cells/mm$^2$) and 10 vol % of FBS/Ham's F-12 was used as the culture solution in place of the 10 vol % FBS/DMEM, and cell proliferation was confirmed. Furthermore, after culturing until the cultured cells covered 100% of the substrate, by cooling the substrate to 10° C., 70% of the cells were detached after 15 minutes.

Reference Example 4

[Cell Culture Evaluation]

Cell culture evaluation was performed for 5 days in the same manner as in the section [Cell Culture Evaluation and Separation Evaluation] of Example 1, except that the cell culture substrate having a membrane comprising the partial block copolymer comprising the 2-methacryloyloxyethyl phosphorylcholine polymer block (B) and the n-butyl methacrylate polymer block (C) introduced onto the surface thereof prepared in the section [Membrane Evaluation] of Reference Example 3 was used, Chinese hamster ovary-derived CHO cells (100 cells/mm$^2$) were used in place of murine connective tissue L929 cells (100 cells/mm$^2$) and 10 vol % of FBS/Ham's F-12 was used as the culture solution in place of the 10 vol % FBS/DMEM. The cells did not adhere to the substrate and proliferation could not be confirmed.

Example 5 (Production by Click Chemistry Reaction)

[Production of n-Butyl Methacrylate Polymer Block Having Terminal Alkynyl Group]

0.57 g (1.8 mmol) of a propargyl ester of 4-cyanopentanoic acid dithiobenzoate, 12.80 g (90 mmol) of n-butyl methacrylate, and 60 mg (0.36 mmol) of azobis(isobutyronitrile) were added to a 200 mL test tube having a three-way valve, and thereafter, 45 mL of 1,4-dioxane and 45 mL of ethanol were added thereto and the components were dissolved. The test tube was immersed in liquid nitrogen, frozen, degassed with a vacuum pump, and returned to room temperature. This operation was repeated three times to remove dissolved oxygen in the test tube. The test tube was heated to 65° C. and polymerization was carried out at 65° C. for 24 hours. After completion of the reaction, the reaction solvent was distilled off under reduced pressure on a rotary evaporator to concentrate the reaction solution. The concentrate was poured into 300 mL of methanol, and a red oily substance settled on the bottom thereof was recovered. Washing was performed twice with 100 mL of methanol, and the obtained oily substance was vacuum-dried to obtain 12.11 g of an n-butyl methacrylate polymer block (C) having a terminal alkynyl group. Using GPC, the number average molecular weight (Mn) and the molecular weight distribution (Mw/Mn) of the obtained polymer were determined and were Mn=6,850 and Mw/Mn=1.14.

[Production of Partial Block Copolymer Having Terminal Alkynyl Group]

5.95 g (0.7 mmol) of the n-butyl methacrylate polymer block (C) having a terminal alkynyl group, 15.84 g (140 mmol) of N-isopropylacrylamide, and 11.5 mg (0.07 mmol) of azobis(isobutyronitrile) were added to a 300 mL test tube having a three-way vale, and thereafter, 140 mL of 1,4-dioxane was added thereto and the components were dissolved. The test tube was immersed in liquid nitrogen, frozen, degassed with a vacuum pump, and returned to room temperature. This operation was repeated three times to remove dissolved oxygen in the test tube. The test tube was heated to 65° C. and polymerization was carried out at 65° C. for 43 hours. After completion of the reaction, the reaction solvent was distilled off under reduced pressure on a rotary evaporator to concentrate the reaction solution. The concentrate was poured into 1000 mL of hexane, and a red precipitate was recovered. Washing was performed twice with 500 mL of hexane, and the obtained red substance was vacuum-dried to obtain 15.26 g of a partial block copolymer including a terminal alkynyl group comprising an N-isopropylacrylamide polymer block (A) and the n-butyl methacrylate polymer block (C). Using GPC, the number average molecular weight (Mn) and the molecular weight distribution (Mw/Mn) of the obtained polymer were determined and were Mn=21,400 and Mw/Mn=1.20.

[Production of Polymer Block (B) Having Terminal Azide Group]

0.20 g (0.57 mmol) of a 3-azidopropyl ester of 4-cyanopentanoic acid dithiobenzoate, 12.01 g (40 mmol) of polyethylene glycol methacrylate (i=4.5, j=0. R$^{16}$=methyl group) (manufactured by Aldrich, Mn=300), and 18.8 mg (0.11 mmol) of azobis(isobutyronitrile) were added to a 200 mL test tube having a three-way valve, and thereafter, 28 mL of 1,4-dioxane was added thereto and the components were dissolved. The test tube was immersed in liquid nitrogen, frozen, degassed with a vacuum pump, and returned to room temperature. This operation was repeated three times to remove dissolved oxygen in the test tube. The test tube was heated to 65° C. and polymerization was carried out at 65° C. for 2.5 hours. After completion of the reaction, the reaction solvent was distilled off under reduced pressure on a rotary evaporator to concentrate the reaction solution. The concentrate was poured into 500 mL of hexane, and a red oily substance settled on the bottom thereof was recovered. Washing was performed twice with 300 mL of hexane, and the obtained red oily substance was vacuum-dried to obtain 5.50 g of a polyethylene glycol methacrylate polymer block (B) including a terminal azide group. Using GPC, the number average molecular weight (Mn) and the molecular weight distribution (Mw/Mn) of the obtained polymer were determined and were Mn=11,400 and Mw/Mn=1.14. The formula weight of the hydrophilic moieties in the repeating units of the polyethylene glycol methacrylate polymer block (B) were a total of 10 carbon, 18 hydrogen, and 6.5 oxygen (242.2). The total formula weight of the repeating unit was 298.4 and the HLB value (as determined by the Griffin method) was 16.

[Block Copolymer Production]

0.50 g of the partial block copolymer having a terminal alkynyl group comprising the N-isopropylacrylamide polymer block (A) and the n-butyl methacrylate polymer block (C) and 0.94 g of the polyethylene glycol methacrylate polymer block (B) having a terminal azide group were added to a 50 mL test tube having a three-way valve and nitrogen substitution was carried out. 9 mL of DMF which had been nitrogen bubbled was added thereto and the components were dissolved. A solution comprising 38 mg of copper (I) bromide. 84 mg of 2,2'-bipyridyl, and 1 mL of DMF, which was prepared separately, was added to the test tube under a nitrogen flow and reaction was carried out at room temperature for 48 hours. After the reaction was complete, the three-way valve was removed, and the copper catalyst was inactivated by contact with air. The reaction solution was passed through a column packed with activated alumina to remove the copper catalyst, and the solution was concentrated with a rotary evaporator. The concentrate was slowly poured into 50 mL of pure water, and the precipitated solids were recovered by centrifugation (3000 rpm×3 min). The obtained solid content was dissolved with 2 mL of methanol and slowly poured again into 50 mL of pure water, and the precipitated solids were recovered by centrifugation (3000 rpm×3 minutes). 0.27 g of a block copolymer comprising the polyethylene glycol methacrylate polymer block (B), the n-butyl methacrylate polymer block (C), and the N-isopropylacrylamide polymer block (A) was obtained by vacuum drying. The composition, Mn, and Mw/Mn of the obtained block copolymer are shown in Table 1.

[Surface Treatment Agent Preparation]

Preparation was performed by the same method as in the section [Surface Treatment Agent Preparation] of Example 1, except that the above block copolymer was used, to prepare a surface treatment agent.

[Membrane Evaluation]

Preparation of a cell culture substrate was performed by the same method as the method described in the section [Membrane Evaluation] of Example 1, except that the above surface treatment agent was used, to prepare a cell culture substrate having the block copolymer comprising the polyethylene glycol methacrylate polymer block (B), the n-butyl methacrylate polymer block (C), and the N-isopropylacrylamide polymer block (A) introduced onto the surface thereof. The membrane thickness was 95 nm. The water contact angles at 40° C. and 20° C. are shown in Table 1. The water contact angle at 20° C. was lower than the water contact angle at 40° C. and was less than 40°, indicating high hydrophilicity.

[Cell Culture Evaluation and Separation Evaluation]

Evaluation was performed in the same manner as in the section [Cell Culture Evaluation and Separation Evaluation] of Example 1, except that the cell culture substrate having the block copolymer comprising the polyethylene glycol methacrylate polymer block (B), the n-butyl methacrylate polymer block (C), and the N-isopropylacrylamide polymer block (A) introduced onto the surface thereof prepared as described above was used, and cell proliferation was confirmed. After culturing until the cultured cells covered 100% of the substrate, by cooling the substrate to 10° C., 100% of the cells were detached after 15 minutes.

Example 6 (Production by Click Chemistry Reaction)

[Production of Polymer Block (B) Having Terminal Azide Group]

0.20 g (0.57 mmol) of a 3-azidopropyl ester of 4-cyanopentanoic acid dithiobenzoate, 6.28 g (40 mmol) of 2-dimethylaminoethyl methacrylate, and 18.8 mg (0.11 mmol) of azobis(isobutyronitrile) were added to a 200 mL test tube having a three-way valve, and thereafter, 28 mL of 1,4-dioxane was added thereto and the components were dissolved. The test tube was immersed in liquid nitrogen, frozen, degassed with a vacuum pump, and returned to room temperature. This operation was repeated three times to remove dissolved oxygen in the test tube. The test tube was heated to 65° C. and polymerization was carried out at 65° C. for 8 hours. After completion of the reaction, the reaction solvent was distilled off under reduced pressure on a rotary evaporator to concentrate the reaction solution. The concentrate was poured into 400 mL of hexane, and a red oily substance settled on the bottom thereof was recovered. Washing was performed twice with 300 mL of hexane, and the obtained red oily substance was vacuum-dried to obtain 3.71 g of a 2-dimethylaminoethyl methacrylate polymer block (B) having a terminal azide group. Using GPC, the number average molecular weight (Mn) and the molecular weight distribution (Mw/Mn) of the obtained polymer were determined and were Mn=7.000 and Mw/Mn=1.12. The formula weight of the hydrophilic moieties in the repeating units of the 2-dimethylaminoethyl methacrylate polymer block (B) are a total of 3 carbon, 4 hydrogen, 1 nitrogen, and 2 oxygen (86.1). The total formula weight of the repeating unit is 157.2 and the HLB value (as determined by the Griffin method) is 11.

[Block Copolymer Production]

Synthesis was performed by the same method as in the section [Block Copolymer Synthesis] of Example 5, except that 0.60 g of the above 2-dimethylaminoethyl methacrylate polymer block (B) having a terminal azide group was used in place of the 0.94 g of the polyethylene glycol methacrylate polymer block (B) having a terminal azide group, to obtain 0.20 g of a block copolymer comprising the 2-dimethylaminoethyl methacrylate polymer block (B), an n-butyl methacrylate polymer block (C), and an N-isopropylacrylamide polymer block (A). The composition, Mn, and Mw/Mn of the obtained block copolymer are shown in Table 1.

[Surface Treatment Agent Preparation]

Preparation was performed by the same method as in the section [Surface Treatment Agent Preparation] of Example 1, except that the above block copolymer was used, to prepare a surface treatment agent.
[Membrane Evaluation]
Preparation of a cell culture substrate was performed by the same method as the method described in the section [Membrane Evaluation] of Example 1, except that the above surface treatment agent was used, to prepare a cell culture substrate having the block copolymer comprising the 2-dimethylaminoethylmethacrylate polymer block (B), the n-butyl methacrylate polymer block (C), and the N-isopropylacrylamide polymer block (A) introduced onto the surface thereof. The membrane thickness was 80 nm. The water contact angles at 40° C. and 20° C. are shown in Table 1. The water contact angle at 20° C. was lower than the water contact angle at 40° C. and was less than 40°, indicating high hydrophilicity.
[Cell Culture Evaluation and Separation Evaluation]
Evaluation was performed in the same manner as in the section [Cell Culture Evaluation and Separation Evaluation] of Example 1, except that the cell culture substrate having the block copolymer comprising the 2-dimethylaminoethyl-methacrylate polymer block (B), the n-butyl methacrylate polymer block (C), and the N-isopropylacrylamide polymer block (A) introduced onto the surface thereof prepared as described above was used, and cell proliferation was confirmed. After culturing until the cultured cells covered 100% of the substrate, by cooling the substrate to 10° C., 100% of the cells were detached after 15 minutes.

Example 7 (Production by Click Chemistry Reaction)

[Production of Polymer Block (B) Having Terminal Azide Group]
0.20 g (0.57 mmol) of a 3-azidopropyl ester of 4-cyanopentanoic acid dithiobenzoate. 5.20 g (40 mmol) of 2-methoxyethyl acrylate, and 18.8 mg (0.11 mmol) of azobis(isobutyronitrile) were added to a 200 mL test tube having a three-way valve, and thereafter, 28 mL of 1,4-dioxane was added thereto and the components were dissolved. The test tube was immersed in liquid nitrogen, frozen, degassed with a vacuum pump, and returned to room temperature. This operation was repeated three times to remove dissolved oxygen in the test tube. The test tube was heated to 65° C. and polymerization was carried out at 65° C. for 9 hours. After completion of the reaction, the reaction solvent was distilled off under reduced pressure on a rotary evaporator to concentrate the reaction solution. The concentrate was poured into 600 mL of hexane, and a red oily substance settled on the bottom thereof was recovered. Washing was performed twice with 300 mL of hexane, and the obtained red oily substance was vacuum-dried to obtain 2.48 g of a 2-methoxyethyl acrylate polymer block (B) having a terminal azide group. Using GPC, the number average molecular weight (Mn) and the molecular weight distribution (Mw/Mn) of the obtained polymer were determined and were Mn=8,100 and Mw/Mn=1.09. The formula weight of the hydrophilic moieties in the repeating units of the 2-methoxyethyl acrylate polymer block (B) are a total of 3 carbon, 4 hydrogen, and 3 oxygen (88.1). The total formula weight of the repeating unit is 130.1 and the HLB value (as determined by the Griffin method) is 14.
[Block Copolymer Production]
Production was performed by the same method as in the section [Block Copolymer Production] of Example 5, except that 0.66 g of the above 2-methoxyethyl acrylate polymer block (B) having a terminal azide group was used in place of the 0.94 g of the polyethylene glycol methacrylate polymer block (B) having a terminal azide group, to obtain 0.23 g of a block copolymer comprising the 2-methoxyethyl acrylate polymer block (B), an n-butyl methacrylate polymer block (C), and an N-isopropylacrylamide polymer block (A). The composition, Mn, and Mw/Mn of the obtained block copolymer are shown in Table 1.
[Surface Treatment Agent Preparation]
Preparation was performed by the same method as in the section [Surface Treatment Agent Preparation] of Example 1, except that the above block copolymer was used, to prepare a surface treatment agent.
[Membrane Evaluation]
Preparation of a cell culture substrate was performed by the same method as the method described in the section [Membrane Evaluation] of Example 1, except that the above surface treatment agent was used, to prepare a cell culture substrate having the block copolymer comprising the 2-methoxyethyl acrylate polymer block (B), the n-butyl methacrylate polymer block (C), and the N-isopropylacrylamide polymer block (A) introduced onto the surface thereof. The membrane thickness was 48 nm. The water contact angles at 40° C. and 20° C. are shown in Table 1. The water contact angle at 20° C. was lower than the water contact angle at 40° C. and was less than 40°, indicating high hydrophilicity.
[Cell Culture Evaluation and Separation Evaluation]
Evaluation was performed in the same manner as in the section [Cell Culture Evaluation and Separation Evaluation] of Example 1, except that the cell culture substrate having the block copolymer comprising the 2-methoxyethyl acrylate polymer block (B), the n-butyl methacrylate polymer block (C), and the N-isopropylacrylamide polymer block (A) introduced onto the surface thereof prepared as described above was used, and cell proliferation was confirmed. After culturing until the cultured cells covered 100% of the substrate, by cooling the substrate to 10° C., 80% of the cells were detached after 15 minutes.

Example 8 (Production by Click Chemistry Reaction)

[Production of Styrene Polymer Block Having Terminal Alkynyl Group]
0.10 g (0.49 mmol) of a propargyl ester of 2-bromoisobutyric acid, 9.37 g (90 mmol) of styrene, 94 mg (0.6 mmol) of 2,2'-bipyridyl, 25 mg (0.25 mmol) of copper (I) chloride, and 25 mg (0.13 mmol) of ascorbic acid were added to a 200 mL test tube having a three-way valve, and thereafter, 90 mL of 1,4-dioxane was added thereto and the components were dissolved. The test tube was immersed in liquid nitrogen, frozen, degassed with a vacuum pump, and returned to room temperature. This operation was repeated three times to remove dissolved oxygen in the test tube. The test tube was heated to 65° C. and polymerization was carried out at 65° C. for 24 hours. After completion of the reaction, the reaction solvent was distilled off under reduced pressure on a rotary evaporator to concentrate the reaction solution. The concentrate was poured into 300 mL of methanol, and an oily substance settled on the bottom thereof was recovered. Washing was performed twice with 100 mL of methanol, and the obtained oily substance was vacuum-dried to obtain a styrene polymer block (C) having a terminal alkynyl group. Using GPC, the number average molecular weight (Mn) and the molecular weight distribution (Mw/Mn) of the obtained polymer were determined and were Mn=19,000 and Mw/Mn=1.14. No hydrophilic moieties were present in the repeating units of the styrene polymer block (C) and the HLB value (as determined by the Griffin method) was 0.

[Production of Partial Block Copolymer Having Terminal Alkynyl Group]

6.0 g of the styrene polymer block (C) having a terminal alkynyl group, 8.7 g (75 mmol) of 2-ethoxyethyl vinyl ether, 94 mg (0.6 mmol) of 2,2'-bipyridyl, 25 mg (0.25 mmol) of copper (I) chloride, and 25 mg (0.13 mmol) of ascorbic acid were added to a 300 mL test tube having a three-way valve, and thereafter, 27 mL of isopropyl alcohol and 63 mL of water were added thereto and the components were dissolved. The test tube was immersed in liquid nitrogen, frozen, degassed with a vacuum pump, and returned to room temperature. This operation was repeated three times to remove dissolved oxygen in the test tube. The test tube was heated to 65° C. and polymerization was carried out at 65° C. for 43 hours. After completion of the reaction, the reaction solvent was distilled off under reduced pressure on a rotary evaporator to concentrate the reaction solution. The concentrate was poured into 1,000 mL of methanol, and the precipitate was recovered. Washing was performed twice with 500 mL of methanol, and the obtained precipitate was vacuum-dried to obtain a partial block copolymer having a terminal alkynyl group comprising a 2-ethoxyethylvinyl ether polymer block (A) and the styrene polymer block (C). Using GPC, the number average molecular weight (Mn) and the molecular weight distribution (Mw/Mn) of the obtained polymer were determined and were Mn=55,000 and Mw/Mn=1.20.

[Production of Polymer Block (B) Having Terminal Azide Group]

0.20 g (0.57 mmol) of a 3-azidopropyl ester of 4-cyanopentanoic acid dithiobenzoate, 11.1 g (40 mmol) of dimethyl(3-methacryloylaminopropyl)(3-sulfonatopropyl)aminium, and 18.8 mg (0.11 mmol) of azobis(isobutyronitrile) were added to a 200 mL test tube having a three-way valve, and thereafter, 28 mL of 1,4-dioxane was added thereto and the components were dissolved. The test tube was immersed in liquid nitrogen, frozen degassed with a vacuum pump, and returned to room temperature. This operation was repeated three times to remove dissolved oxygen in the test tube. The test tube was heated to 65° C. and polymerization was carried out at 65° C. for 9 hours. After completion of the reaction, the reaction solvent was distilled off under reduced pressure on a rotary evaporator to concentrate the reaction solution. The concentrate was poured into 600 mL of hexane, and a red oily substance settled on the bottom thereof was recovered. Washing was performed twice with 300 mL of hexane, and the obtained red oily substance was vacuum-dried to obtain 2.48 g of a dimethyl(3-methacryloylaminopropyl)(3-sulfonatopropyl)aminium polymer block (B) having a terminal azide group. Using GPC, the number average molecular weight (Mn) and the molecular weight distribution (Mw/Mn) of the obtained polymer were determined and were Mn=17,300 and Mw/Mn=1.09. The formula weight of the hydrophilic moieties in the repeating units of the dimethyl(3-methacryloylaminopropyl)(3-sulfonatopropyl)aminium polymer block (B) are a total of 3 carbon, 5 hydrogen, 2 nitrogen, 4 oxygen, and 1 sulfur (165.1). The total formula weight of the repeating unit is 292.4 and the HLB value (as determined by the Griffin method) is 11.

[Block Copolymer Production]

0.50 g of the partial block copolymer having a terminal alkynyl group comprising the 2-ethoxyethyl vinyl ether polymer block (A) and the styrene polymer block (C) (HLB value (as determined by the Griffin method)=0) and 0.94 g of the dimethyl(3-methacryloylaminopropyl)(3-sulfonatopropyl)aminium polymer block (B) having a terminal azide group were added to a 50 mL test tube having a three-way valve and nitrogen substitution was carried out. 9 mL of DMF which had been nitrogen bubbled was added thereto and the components were dissolved. A solution comprising 38 mg of copper (I) bromide, 84 mg of 2,2'-bipyridyl, and 1 mL of DMF, which was prepared separately, was added to the test tube under a nitrogen flow and reaction was carried out at room temperature for 48 hours. After the reaction was complete, the three-way valve was removed, and the copper catalyst was inactivated by contact with air. The reaction solution was passed through a column packed with activated alumina to remove the copper catalyst, and the solution was concentrated with a rotary evaporator. The concentrate was slowly poured into 50 mL of pure water, and the precipitated solids were recovered by centrifugation (3000 rpm×3 min). The obtained solid content was dissolved with 2 mL of methanol and slowly poured again into 50 mL of pure water, and the precipitated solids were recovered by centrifugation (3000 rpm×3 minutes). 0.27 g of a block copolymer comprising the dimethyl(3-methacryloylaminopropyl)(3-sulfonatopropyl)aminium polymer block (B), the styrene polymer block (C), and the 2-ethoxyethyl vinyl ether polymer block (A) was obtained by vacuum drying. The composition, Mn, and Mw/Mn of the obtained block copolymer are shown in Table 1.

[Surface Treatment Agent Preparation]

Preparation was performed by the same method as in the section [Surface Treatment Agent Preparation] of Example 1, except that the above block copolymer was used, to prepare a surface treatment agent.

[Membrane Evaluation]

Preparation of a cell culture substrate was performed by the same method as the method described in the section [Membrane Evaluation] of Example 1, except that the above surface treatment agent was used, to prepare a cell culture substrate having the block copolymer comprising the dimethyl(3-methacryloylaminopropyl)(3-sulfonatopropyl)aminium polymer block (B), the styrene polymer block (C), and the 2-ethoxyethyl vinyl ether polymer block (A) introduced onto the surface thereof. The membrane thickness was 45 nm. The water contact angles at 40° C. and 20° C. are shown in Table 1. The water contact angle at 20° C. was lower than the water contact angle at 40° C. and was less than 40°, indicating high hydrophilicity.

[Cell Culture Evaluation and Separation Evaluation]

Evaluation was performed in the same manner as in the section [Cell Culture Evaluation and Separation Evaluation] of Example 1, except that the cell culture substrate having the block copolymer comprising the dimethyl(3-methacryloylaminopropyl)(3-sulfonatopropyl)aminium polymer block (B), the styrene polymer block (C), and the 2-ethoxyethyl vinyl ether polymer block (A) introduced onto the surface thereof prepared as described above was used, and cell proliferation was confirmed. After culturing until the cultured cells covered 100% of the substrate, by cooling the substrate to 10° C., 72% of the cells were detached after 15 minutes.

Example 9 (Production by Click Chemistry Reaction)

[Production of Partial Block Copolymer Having Terminal Alkynyl Group]

Production was performed by the same method as in the section [Production of Partial Block Copolymer Having Terminal Alkynyl Group] of Example 8, except that 4.4 g (75 mmol) of methyl vinyl ether was used in place of the 8.7 g (75 mmol) of 2-ethoxyethyl vinyl ether, to obtain a partial block copolymer having a terminal alkynyl group comprising a methyl vinyl ether polymer block (A) and a styrene polymer block (C). Using GPC, the number average molecular weight (Mn) and the molecular weight distribution (Mw/Mn) of the obtained polymer were determined and were Mn=51,000 and Mw/Mn=1.20.

[Block Copolymer Production]

Production was performed by the same method as in the section [Block Copolymer Production] of Example 8, except that 0.45 g of the partial block copolymer having a terminal alkynyl group comprising the methyl vinyl ether polymer block (A) and the styrene polymer block (C) was used in place of the 0.50 g of the partial block copolymer having a terminal alkynyl group comprising the 2-ethoxyethyl vinyl ether polymer block (A) and the styrene polymer block (C), to obtain 0.20 g of a block copolymer comprising a dimethyl (3-methacryloylaminopropyl)(3-sulfonatopropyl)aminium polymer block (B), the styrene polymer block (C), and the methyl vinyl ether polymer block (A). The composition, Mn, and Mw/Mn of the obtained block copolymer are shown in Table 1.

[Surface Treatment Agent Preparation]

Preparation was performed by the same method as in the section [Surface Treatment Agent Preparation] of Example 1, except that the above block copolymer was used, to prepare a surface treatment agent.

[Membrane Evaluation]

Preparation of a cell culture substrate was performed by the same method as the method described in the section [Membrane Evaluation] of Example 1, except that the above surface treatment agent was used, to prepare a cell culture substrate having the block copolymer comprising a dimethyl (3-methacryloylaminopropyl)(3-sulfonatopropyl)aminium polymer block (B), the styrene polymer block (C), and the methyl vinyl ether polymer block (A) introduced onto the surface thereof. The membrane thickness was 45 nm. The water contact angles at 40° C. and 20° C. are shown in Table 1. The water contact angle at 20° C. was lower than the water contact angle at 40° C. and was less than 40°, indicating high hydrophilicity.

[Cell Culture Evaluation and Separation Evaluation]

Evaluation was performed in the same manner as in the section [Cell Culture Evaluation and Separation Evaluation] of Example 1, except that the cell culture substrate having the block copolymer comprising a dimethyl(3-methacryloylaminopropyl)(3-sulfonatopropyl)aminium polymer block (B), the styrene polymer block (C), and the methyl vinyl ether polymer block (A) introduced onto the surface thereof prepared as described above was used, and cell proliferation was confirmed. Furthermore, after culturing until the cultured cells covered 100% of the substrate, by cooling the substrate to 10° C., 73% of the cells were detached after 15 minutes.

Comparative Example 1

[Membrane Evaluation]

The water contact angles at 40° C. and 20° C. of a 35 mm φ UpCell® dish manufactured by Cell Seed Co., Ltd., are shown in Table 1. The water contact angle at 20° C. was higher than 40°, and the dish was found to be less hydrophilic at 20° C. than the culture substrate of the present invention.

[Cell Culture Evaluation and Separation Evaluation]

Evaluation was performed in the same manner as in the section [Cell Culture Evaluation and Separation Evaluation] of Example 1, except that the above 35 mm φ UpCell® dish manufactured by Cell Seed Co., Ltd., was used, and cell proliferation was confirmed. In the cell separation evaluation after cell proliferation, by cooling for 3 minutes. 30% of cells were detached. By cooling for 15 minutes, 65% of cells were detached.

Comparative Example 2

[Production of Polymer Block (C)]

2.240 g of n-butyl methacrylate, 0.073 g of 4-cyano-4-[(dodecylsulfonylthiocarbonyl) sulfonyl] pentanoic acid as a RAFT agent, and 0.004 g of azobis(isobutyronitrile) were added to a 100 mL two-neck eggplant-type flask, and thereafter, 10 mL of 1,4-dioxne was added thereto and the components were dissolved. After nitrogen bubbling was carried out for 30 minutes, reaction was carried out for 12 hours at 65° C. After reaction, the mixture was reprecipitated with methanol to obtain an n-butyl methacrylate polymer block (C).

[Partial Block Copolymer Production]

1.200 g of the n-butyl methacrylate polymer block (C), 1.210 g of N-isopropylacrylamide, and 0.004 g of azobis (isobutyronitrile) were added to a 100 mL two-neck eggplant-type flask, and thereafter, 15 mL of a 1:2 mixed solution of 1,4-dioxane/ethanol was added thereto and the components were dissolved. After nitrogen bubbling was carried out for 30 minutes, reaction was carried out for 12 hours at 65° C. After reaction, the mixture was reprecipitated with pure water to obtain a partial block copolymer comprising the n-butyl methacrylate polymer block (C) and an N-isopropylacrylamide polymer block (A).

[Surface Treatment Agent Preparation]

Preparation was performed by the same method as in the section [Surface Treatment Agent Preparation] of Example 1, except that the above partial block copolymer was used, to prepare a surface treatment agent.

[Membrane Evaluation]

Preparation of a cell culture substrate was performed by the same method as described in the section [Membrane Evaluation] of Example 1, except that the above surface treatment agent was used, to prepare a cell culture substrate having the partial block copolymer comprising the n-butyl methacrylate polymer block (C) and the N-isopropylacrylamide polymer block (A) introduced onto the surface thereof. The membrane thickness was 100 nm. The water contact angles at 40° C. and 20° C. are shown in Table 1. The water contact angle at 20° C. was higher than 40°, and the substrate was found to be less hydrophilic at 20° C. than the culture substrate of the present invention.

[Cell Culture Evaluation and Separation Evaluation]

Evaluation was performed in the same manner as in the section [Cell Culture Evaluation and Separation Evaluation] of Example 1, except that the cell culture substrate having the temperature responsive membrane introduced onto the surface thereof prepared as described above was used, and cell proliferation was confirmed. In the cell separation evaluation after cell proliferation, by cooling for 3 minutes, 24% of cells were detached. By cooling for 15 minutes, 60% of cells were detached.

Comparative Example 3

[Surface Treatment Agent Preparation]

Preparation was performed by the same method as in the section [Surface Treatment Agent Preparation] of Example 1, except that the partial block copolymer synthesized in the section [Production of Partial Block Copolymer Having Terminal Alkynyl Group] of Example 5 was used.

[Membrane Evaluation]

Preparation of a cell culture substrate was performed by the same method as the method described in the section [Membrane Evaluation] of Example 1, except that the above surface treatment agent was used, to prepare a cell culture substrate having a partial block copolymer comprising an n-butyl methacrylate polymer block (C) and an N-isopropylacrylamide polymer block (A) introduced onto the surface thereof. The membrane thickness was 80 nm. The water contact angles at 40° C. and 20° C. are shown in Table 1. The water contact angle at 20° C. was higher than 40°, and the substrate was found to be less hydrophilic at 20° C. than the culture substrate of the present invention.

[Cell Culture Evaluation and Separation Evaluation]

Evaluation was performed in the same manner as in the section [Cell Culture Evaluation and Separation Evaluation] of Example 1, except that the above cell culture substrate having the temperature-responsive membrane introduced onto the surface thereof prepared as described above was used, and cell proliferation was confirmed. In the cell separation evaluation after cell proliferation, by cooling for 3 minutes, 26% of cells were detached. By cooling for 15 minutes, 63% of cells were detached.

Comparative Example 4

[Membrane Evaluation]

The water contact angles at 40° C. and 20° C. of a cell culture treated 35 mm φ dish manufactured by Corning Inc., are shown in Table 1. The water contact angles at 40° C. and 20° C. were the same angle (48°) and the dish exhibited no temperature-responsiveness.

[Cell Culture Evaluation and Separation Evaluation]

Evaluation was performed in the same manner as in the section [Cell Culture Evaluation and Separation Evaluation] of Example 1, except that the above cell culture treated 35 mm φ dish manufactured by Corning Inc., was used, and cell proliferation was confirmed. In the cell separation evaluation after cell proliferation, even after cooling for 15 minutes none of the cells were detached.

Example 10

[Production of Polymer Block (B)]

2.4 g (16.0 mmol) of 2-dimethylaminoethyl methacrylate, 108 mg (267 μmol) of 4-cyano-4-[(dodecylsulfonylthiocarbonyl)sulfonyl] pentanoic acid as a RAFT agent, and 8.8 mg (53 μmol) of azobis(isobutyronitrile) as an initiator were added to a 100 mL test tube having a three-way valve, and thereafter, 10 mL of 1,4-dioxane was added thereto and the components were dissolved. After argon bubbling was carried out for 10 minutes, reaction was carried out for 29 hours at 65° C. After reaction, a part of the reaction solution was collected and measured by $^1$H-NMR, and as a result, it was confirmed that 93% of the charged amount of 2-dimethylaminoethyl methacrylate had polymerized, whereby a polymer of 2-dimethylaminoethyl methacrylate (polymer block (B)) was produced.

[Partial Block Copolymer Production]

10 mL of 1,4-dioxane, 2.4 g (16.9 mmol) of n-butyl methacrylate, and 8.8 mg (53 μmol) of azobis(isobutyronitrile) were added to the reaction solution obtained as described above, and after argon bubbling was carried out for 10 minutes, reaction was carried out for 25 hours at 65° C. After reaction, a part of the reaction solution was collected and measured by $^1$H-NMR, and as a result, it was confirmed that 92% of the charged amount of the n-butyl methacrylate had polymerized, whereby a partial block copolymer comprising the 2-dimethylaminoethyl methacrylate polymer (B) and an n-butyl methacrylate polymer block (C) was produced.

[Block Copolymer Production]

20 mL of 1,4-dioxane, 4.8 g (42.4 mmol) of N-isopropylacrylamide, and 8.8 mg (53 μmol) of azobis(isobutyronitrile) were added to the reaction solution obtained as described above, and after argon bubbling was carried out for 10 minutes, reaction was carried out for 45 hours at 65° C. After reaction, a part of the reaction solution was collected and measured by $^1$H-NMR, and as a result, it was confirmed that 99% of the charged amount of the N-isopropylacrylamide had polymerized. The reaction solution was poured into 300 mL of distilled water, and a precipitated white solid was filtered. The obtained white solid was dissolved in 300 mL of chloroform, 5 g of anhydrous magnesium sulfate was added to the obtained solution, and the mixture was stirred at room temperature for 30 minutes. The resulting suspension was filtered to remove the magnesium sulfate, and the chloroform was distilled off from the filtrate under reduced pressure using an evaporator to concentrate to 30 mL. The obtained concentrated solution was poured into 300 mL of hexane, and the precipitated white solid was filtered. The obtained white solid was dried under reduced pressure at 80° C. for 6 hours to obtain 5.8 g of a block copolymer comprising the 2-dimethylaminoethyl methacrylate polymer (B), the n-butyl methacrylate polymer block (C), and an N-isopropylacrylamide polymer block (A) as a white powder. The composition, Mn, and Mw/Mn of the obtained block copolymer are shown in Table 2.

[Surface Treatment Agent Preparation]

A 0.5 wt % surface treatment agent was prepared by dissolving 150 mg of the above block copolymer in 29.85 g of ethanol.

[Membrane Evaluation]

The obtained surface treatment agent was added in 1 mL increments to an IWAKI 100 mm φ dish for tissue culture, allowed to stand at room temperature for 5 minutes, and thereafter, the added surface treatment agent was collected with a Pasteur pipette. After the dish was allowed to stand at room temperature for 1 hour and the surface of the dish dried, the dish was heated in an oven set to 70° C. for 1 hour to prepare a cell culture substrate having a membrane formed from the block copolymer comprising the 2-dimethylaminoethyl methacrylate polymer (B), the n-butyl methacrylate polymer block (C), and an N-isopropylacrylamide polymer block (A) introduced onto the surface thereof. The membrane thickness was 10 nm. The water contact angles at 40° C. and 20° C. are shown in Table 2. The water contact angle at 20° C. was lower than the water contact angle at 40° C. and was less than 40°, indicating high hydrophilicity.

[Cell Culture Evaluation and Separation Evaluation]

Human bone marrow-derived mesenchymal stem cells (Lonza Inc., PT-2501) (100 cells/mm$^2$) were cultured at 37° C. at a 5% $CO_2$ concentration using the cell culture substrate having a membrane formed from the block copolymer comprising the 2-dimethylaminoethyl methacrylate polymer (B), the n-butyl methacrylate polymer block (C), and an N-isopropylacrylamide polymer block (A) introduced onto the surface thereof prepared as described above. A Lonza PT-3001 kit was used as the medium and a cofactor. Cell proliferation was confirmed and the cells were cultured until the cultured cells covered 100% of the substrate, and thereafter, the number of cells was confirmed with a 10×10 magnification microscope. After cooling the substrate to 10° C., detached cells were removed with an aspirator, and the number of cells was again confirmed with a 10×10 magnification microscope. By cooling for 15 minutes, 100% of the cells were detached in the form of single cells.

Example 11

[Production of Polymer Block (B)]

Production was performed by the same method as in the section [Production of Polymer Block (B)] of Example 10, except that 1.2 g (7.8 mmol) of 2-dimethylaminoethyl methacrylate, 50 mg (123 μmol) of 4-cyano-4-[(dodecylsulfonylthiocarbonyl) sulfonyl] pentanoic acid, and 1.7 mg (10 μmol) of azobis(isobutyronitrile) were used and the reaction was carried out for 25 hours, and it was confirmed by $^1$H-NMR that 86% of the charged amount of the 2-dimethylaminoethyl methacrylate had polymerized, whereby a 2-dimethylaminoethyl methacrylate polymer (polymer block (B)) was produced.

[Partial Block Copolymer Production]

Production was performed by the same method as in the section [Partial Block Copolymer Production] of Example 10, except that 3.7 g (26 mmol) of n-butyl methacrylate and 1.8 mg (11 μmol) of azobis(isobutyronitrile) were used and reaction was carried out for 21 hours, and thereafter it was confirmed by $^1$H-NMR that 95% of the charged amount of the n-butyl methacrylate had polymerized, whereby a partial block copolymer comprising a 2-dimethylaminoethylmethacrylate polymer block (B) and an n-butyl methacrylate polymer block (C) was produced.

[Block Copolymer Production]

Production was performed by the same method as in the section [Block Copolymer Production] of Example 10, except that 4.9 g (43 mmol) of N-isopropylacrylamide and 2 mg (12 μmol) of azobis(isobutyronitrile) were used and the reaction was carried out for 42 hours, whereby it could be confirmed by $^1$H-NMR that 54% of the charged amount of the N-isopropylacrylamide had polymerized. The obtained reaction solution was treated by the same method as the method described in [Block Copolymer Production] of Example 10, whereby 4.4 g of a block copolymer comprising the 2-dimethylaminoethyl methacrylate polymer block (B), the n-butyl methacrylate polymer block (C), and an N-isopropylacrylamide polymer block (A) was obtained as a white powder. The composition, Mn, and Mw/Mn of the obtained block copolymer are shown in Table 2.

[Surface Treatment Agent Preparation]

Preparation was performed by the same method as in the section [Surface Treatment Agent Preparation] of Example 10, except that the above block copolymer was used, to prepare a 0.5 wt % surface treatment agent.

[Membrane Evaluation]

A cell culture substrate was prepared by the same method as described in the section [Membrane Evaluation] of Example 10, except that the above surface treatment agent was used. The membrane thickness was 10 nm. The water contact angles at 40° C. and 20° C. are shown in Table 2. The water contact angle at 20° C. was lower than the water contact angle at 40° C. and was less than 40°, indicating high hydrophilicity.

[Cell Culture Evaluation and Separation Evaluation]

Evaluation was performed by the same method as in the section [Cell Culture Evaluation and Separation Evaluation] of Example 10, except that the cell culture substrate prepared as described above was used. Cell proliferation was confirmed, and after the cells were cultured until the cultured cells covered 100% of the substrate, the number of cells was confirmed with a 10×10 magnification microscope. After the substrate was cooled to 10° C., the detached cells were removed with an aspirator, and the number of cells was again confirmed with a 10×10 magnification microscope. By cooling for 15 minutes, 100% of the cells were detached in the form of single cells.

Example 12

[Cell Culture Evaluation and Separation Evaluation]

Human preadipocyte cells (Toyobo Co., Ltd., CA802s05a) (100 cells/mm$^2$) were cultured at 37° C. at a 5% $CO_2$ concentration using the cell culture substrate having a membrane formed from the block copolymer comprising the 2-dimethylaminoethyl methacrylate polymer block (B), the n-butyl methacrylate polymer block (C), and an N-isopropylacrylamide polymer block (A) introduced onto the surface thereof prepared in the section [Membrane Evaluation] of Example 11. A human preadipocyte cell proliferation medium (Toyobo Co., Ltd., CA811K500) was used as the medium. Cell proliferation was confirmed, and after the cells were cultured until the cultured cells covered 100% of the substrate, the number of cells was confirmed with a 10×10 magnification microscope. After cooling the substrate to 10° C., detached cells were removed with an aspirator, and the number of cells was again confirmed with a 10×10 magnification microscope. By cooling for 15 minutes. 100% of the cells were detached in the form of single cells.

Example 13

[Production of Polymer Block (B)]

0.27 g (1.7 mmol) of 2-dimethylaminoethyl methacrylate, 0.16 g (1.1 mmol) of n-butyl methacrylate. 55 mg (135 μmol) of 4-cyano-4-[(dodecylsulfonylthiocarbonyl) sulfonyl] pentanoic acid as a RAFT agent, and 4.4 mg (27 μmol) of azobis(isobutyronitrile) as an initiator were added to a 100 mL test tube having a three-way valve, and were dissolved in 15 mL of 1,4-dioxane. After argon bubbling was carried out for 10 minutes, reaction was carried out for 40 hours at 65° C. After reaction, a part of the reaction solution was collected and measured by $^1$H-NMR As a result, it was confirmed that 97% of the charged amount of the 2-dimethylaminoethyl methacrylate and 98% of the charged amount of the n-butyl methacrylate had polymerized, whereby a copolymer of 2-dimethylaminoethyl methacrylate and n-butyl methacrylate (2-dimethylaminoethyl methacrylate: 60.1 mol % and n-butyl methacrylate: 39.9 mol %) was produced (copolymer block (B)). The HLB value of the obtained copolymer block (b) is 9.0.

[Partial Block Copolymer Production]

5 mL of 1,4-dioxane, 0.75 g (4.8 mmol) of 2-dimethylaminoethyl methacrylate, 2.89 g (20.3 mmol) of n-butyl methacrylate, and 4.4 mg (27 μmol) of azobis(isobutyronitrile) were added to the copolymer block (B) reaction solution obtained as described above, and after argon bubbling was carried out for 10 minutes, reaction was carried out for 40 hours at 65° C. After reaction, a part of the reaction solution was collected and measured by $^1$H-NMR. As a result, it was confirmed that 97% of the charged amount of the 2-dimethylaminoethyl methacrylate and 98% of the charged amount of the n-butyl methacrylate had polymerized, whereby a partial block copolymer in which a copolymer (copolymer block (C)) of 2-dimethylaminoethyl methacrylate and n-butyl methacrylate (2-dimethylaminoethyl methacrylate: 19 mol % and n-butyl methacrylate: 81 mol %) bonded with the copolymer block (B) was produced. The HLB value of the obtained copolymer block (C) is 7.0.
[Block Copolymer Production]

15 mL of 1,4-dioxane, 3.1 g (27 mmol) of N-isopropylacrylamide, and 4.4 mg (27 µmol) of azobis(isobutyronitrile) were added to the partial block copolymer reaction solution obtained as described above, and after argon bubbling was carried out for 10 minutes, reaction was carried out for 72 hours at 65° C. After reaction, a part of the reaction solution was collected and measured by $^1$H-NMR As a result, it was confirmed that 99% of the charged amount of the N-isopropylacrylamide had polymerized. The reaction solution was poured into 300 mL of distilled water, and a precipitated white solid was filtered. The obtained white solid was dissolved in 300 mL of chloroform, 5 g of anhydrous magnesium sulfate was added to the obtained solution, and the mixture was stirred at room temperature for 30 minutes. The resulting suspension was filtered to remove the magnesium sulfate, and the chloroform was distilled off from the filtrate under reduced pressure using an evaporator to concentrate to 30 mL. The obtained concentrated solution was poured into 300 mL of hexane, and the precipitated white solid was filtered. The obtained white solid was dried under reduced pressure at 80° C. for 6 hours to obtain 3.5 g of a block copolymer comprising the copolymer block (B) of 2-dimethylaminoethyl methacrylate and n-butyl methacrylate, the copolymer block (C) of 2-dimethylaminoethyl methacrylate and n-butyl methacrylate, and an N-isopropylacrylamide polymer block (A) as a white powder. The composition, Mn, and Mw/Mn of the obtained block copolymer are shown in Table 2.
[Surface Treatment Agent Preparation]

A 0.1 wt % surface treatment agent was prepared by dissolving 30 mg of the above block copolymer in 30 g of ethanol.
[Membrane Evaluation]

2 mL of the obtained surface treatment agent was added to an IWAKI 100 mm φ dish for tissue culture, allowed to stand at room temperature for 5 minutes, and thereafter, the extra surface treatment agent that was not dried was collected with a Pasteur pipette. After the dish was allowed to stand at room temperature for 1 hour and the surface of the dish dried, the dish was heated in an oven set to 70° C. for 1 hour to prepare a cell culture substrate having a membrane formed from the block copolymer comprising the copolymer block (B) of 2-dimethylaminoethyl methacrylate and n-butyl methacrylate, the copolymer block (C) of 2-dimethylaminoethyl methacrylate and n-butyl methacrylate, and the N-isopropylacrylamide polymer block (A) introduced onto the surface thereof. The membrane thickness was 10 nm. The water contact angles at 40° C. and 20° C. are shown in Table 2. The water contact angle at 20° C. was lower than the water contact angle at 40° C. and was less than 40°, indicating high hydrophilicity.
[Cell Culture Evaluation and Separation Evaluation]

Human fetal lung-derived normal diploid fibroblast cells (JCRB Cell Bank, TIG-3-20) (100 cells/mm$^2$) were cultured at 37° C. at a 5% $CO_2$ concentration using the cell culture substrate having a membrane formed from the block copolymer comprising the copolymer block (B) of 2-dimethylaminoethyl methacrylate and n-butyl methacrylate, the copolymer block (C) of 2-dimethylaminoethyl methacrylate and n-butyl methacrylate, and the N-isopropylacrylamide polymer block (A) introduced onto the surface thereof prepared as described above. Eagle minimum essential medium (10 vol % FBS/EMEM) containing 10 vol % fetal bovine serum was used as the culture solution. Cell proliferation was confirmed and the cells were cultured until the cultured cells covered 100% of the substrate, and thereafter, the number of cells was confirmed with a 10×10 magnification microscope. After cooling the substrate to 10° C., detached cells were removed with an aspirator, and the number of cells was again confirmed with a 10×10 magnification microscope. By cooling for 15 minutes, 100% of the cells were detached in the form of single cells.

Example 14

[Production of Polymer Block (B)]

Production was performed by the same method as in the section [Production of Polymer Block (B)] of Example 13, except that 1.1 g (7.0 mmol) of 2-dimethylaminoethyl methacrylate and 0.58 g (4.1 mmol) of n-butyl methacrylate were used. After reaction, a part of the reaction solution was collected and measured by $^1$H-NMR. As a result, it was confirmed that 97% of the charged amount of the 2-dimethylaminoethyl methacrylate and 98% of the charged amount of the n-butyl methacrylate had polymerized, whereby a copolymer of 2-dimethylaminoethyl methacrylate and n-butyl methacrylate (2-dimethylaminoethyl methacrylate: 62.9 mol % and n-butyl methacrylate: 37.1 mol %) (copolymer block (B)) was produced. The HLB value of the obtained polymer block (B) is 9.2.
[Partial Block Copolymer Production]

Production was performed by the same method as in the section [Partial Block Copolymer Production] of Example 13, except that the reaction solution obtained as described above and 2.37 g (16.7 mmol) of n-butyl methacrylate were used and the 2-dimethylaminoethyl methacrylate was not added. After reaction, a part of the reaction solution was collected and measured by $^1$H-NMR. As a result, it was confirmed that 98% of the charged amount of the n-butyl methacrylate, whereby a partial block copolymer in which a polymer of n-butyl methacrylate (polymer block (C)) (n-butyl methacrylate: 100 mol %) bonded with the copolymer block (B) was produced.
[Block Copolymer Production]

Production was performed by the same method as in the section [Block Copolymer Production] of Example 13, except that the reaction solution obtained as described above was used. After reaction, a part of the reaction solution was collected and measured by $^1$H-NMR. As a result, it was confirmed that 99% of the charged amount of the N-isopropylacrylamide had polymerized. The obtained reaction solution was treated by the same method as in the section [Block Copolymer Production] of Example 13, whereby 3.0 g of a block copolymer comprising the copolymer block (B) of 2-dimethylaminoethyl methacrylate and n-butyl methacrylate, the polymer block (C) of n-butyl methacrylate, and an N-isopropylacrylamide polymer block (A) was obtained as a white powder. The composition, Mn, and Mw/Mn of the obtained block copolymer are shown in Table 2.
[Surface Treatment Agent Preparation]

Preparation was performed by the same method as in the section [Surface Treatment Agent Preparation] of Example 13, except that the above block copolymer was used, to prepare a 0.1 wt % surface treatment agent.
[Membrane Evaluation]

Preparation was performed by the method described in the section [Membrane Evaluation] of Example 13, except that the above surface treatment agent was used, to prepare a cell culture substrate having a membrane formed from the block copolymer comprising the copolymer block (B) of 2-dimethylaminoethyl methacrylate and n-butyl methacrylate, the polymer block (C) of n-butyl methacrylate, and an N-isopropylacrylamide polymer block (A) introduced onto the surface thereof. The membrane thickness was 10 nm. The water contact angles at 40° C. and 20° C. are shown in Table 2. The water contact angle at 20° C. was lower than the water contact angle at 40° C. and was less than 40°, indicating high hydrophilicity.
[Cell Culture Evaluation and Separation Evaluation]

Evaluation was performed by the same method as in the section [Cell Culture Evaluation and Separation Evaluation] of Example 13 except that the cell culture substrate prepared as described above was used. Cell proliferation was confirmed, and after culturing was performed until the cultured cells covered 100% of the substrate, the number of cells was confirmed with a 10×10 magnification microscope. After the substrate was cooled to 10° C., detached cells were removed with an aspirator, and the number of cells was again confirmed with a 10×10 magnification microscope. By cooling for 15 minutes, 100% of the cells were detached in a sheet form.

Example 15

[Production of Polymer Block (B)]

0.94 g (6.0 mmol) of 2-dimethylaminoethyl methacrylate, 0.90 g (9.0 mmol) of methyl methacrylate, 55 mg (135 µmol) of 4-cyano-4-[(dodecylsulfonylthiocarbonyl) sulfonyl]pentanoic acid as a RAFT agent, and 4.4 mg (27 µmol) of azobis(isobutyronitrile) as an initiator were added to a 100 mL test tube having a three-way valve, and were dissolved in 10 mL of 1,4-dioxane. After argon bubbling was carried out for 10 minutes, reaction was carried out for 40 hours at 65° C. After reaction, a part of the reaction solution was collected and measured by $^1$H-NMR. As a result, it was confirmed that 96% of the charged amount of the 2-dimethylaminoethyl methacrylate and 97% of the charged amount of the methyl methacrylate had polymerized, whereby a copolymer of 2-dimethylaminoethyl methacrylate and methyl methacrylate (2-dimethylaminoethyl methacrylate: 39.8 mol % and methyl methacrylate: 60.2 mol %) (copolymer block (B)) was produced. The formula weight of the hydrophilic moieties of the repeating units generated by polymerizing methyl methacrylate was a total of 1 carbon and 2 oxygen (44.0). The total formula weight of the repeating units was 100.1, and the HLB value thereof (as determined by the Griffin method) was 9. The HLB value (as determined by the Griffin method) of the obtained polymer block (B) is 10.
[Partial Block Copolymer Production]10 mL of 1,4-dioxane, 1.71 g (12.0 mmol) of n-butyl methacrylate, and 4.4 mg of azobis(isobutyronitrile) were added to the reaction solution obtained as described above, and after argon bubbling was carried out for 10 minutes, reaction was carried out for 40 hours at 65° C. After reaction, a part of the reaction solution was collected and measured by $^1$H-NMR. As a result, it was confirmed that 98% of the charged amount of the n-butyl methacrylate had polymerized, whereby a partial block copolymer in which an n-butyl methacrylate polymer (polymer block (C)) bonded with the copolymer block (B) was produced.
[Block Copolymer Production]

Production was performed by the same method as in the section [Block Copolymer Production] of Example 13, except that the reaction solution obtained as described above was used. After reaction, a part of the reaction solution was collected and measured by $^1$H-NMR. As a result, it was confirmed that 99% of the charged amount of the N-isopropylacrylamide had polymerized. The obtained reaction solution was treated by the same method as in the section [Block Copolymer Production] of Example 13, whereby 3.5 g of a block copolymer comprising the copolymer block (B) of 2-dimethylaminoethyl methacrylate and methyl methacrylate, the n-butyl methacrylate polymer block (C), and an N-isopropylacrylamide polymer block (A) was obtained as a white powder. The composition, Mn, and Mw/Mn of the obtained block copolymer are shown in Table 2.
[Surface Treatment Agent Preparation]

Preparation was performed by the same method as in the section [Surface Treatment Agent Preparation] of Example 13, except that the above block copolymer was used, to prepare a 0.1 wt % surface treatment agent.
[Membrane Evaluation]

Preparation was performed by the same method as described in the section [Membrane Evaluation] of Example 13, except that the above surface treatment agent was used, to prepare a cell culture substrate having a membrane formed from the block copolymer comprising the copolymer block (B) of 2-dimethylaminoethyl methacrylate and methyl methacrylate, the n-butyl methacrylate polymer block (C), and the N-isopropylacrylamide polymer block (A) introduced onto the surface thereof. The membrane thickness was 11 nm. The water contact angles at 40° C. and 20° C. are shown in Table 2. The water contact angle at 20° C. was lower than the water contact angle at 40° C. and was less than 40°, indicating high hydrophilicity.
[Cell Culture Evaluation and Separation Evaluation]

Evaluation was performed by the same method as in the section [Cell Culture Evaluation and Separation Evaluation] of Example 13 except that the cell culture substrate prepared as described above was used. Cell proliferation was confirmed, and after culturing was carried out until the cultured cells covered 100% of the substrate, the number of cells was confirmed with a 10×10 magnification microscope. By cooling for 15 minutes, 100% of the cells were detached in a sheet form.

Example 16

[Production of Polymer Block (B)]

0.70 g (5.4 mmol) of 2-methoxyethyl acrylate, 55 mg (135 µmol) of 4-cyano-4-[(dodecylsulfonylthiocarbonyl) sulfonyl] pentanoic acid as a RAFT agent, and 4.4 mg (27 µmol) of azobis(isobutyronitrile) as an initiator were added to a 100 mL test tube having a three-way valve, and were dissolved in 5 mL of 1,4-dioxane. After argon bubbling was carried out for 10 minutes, reaction was carried out for 40 hours at 65° C. After reaction, a part of the reaction solution was collected and measured by $^1$H-NMR. As a result, it was confirmed that 99% of the charged amount of the 2-methoxyethyl acrylate and 98% of the charged amount of the 2-methoxyethyl acrylate had polymerized, whereby a polymer of 2-methoxyethyl acrylate (polymer block (B)) was produced. The formula weight of the hydrophilic moieties of the repeating units of the 2-methoxyethyl acrylate were a total of 3 carbon, 4 hydrogen, and 3 oxygen (88.1). The total formula weight of the repeating units was 130.1, and the HLB value thereof (as determined by the Griffin method) is 14.

[Partial Block Copolymer Production]

15 mL of 1,4-dioxane, 2.76 g (19.4 mmol) of n-butyl methacrylate, and 4.4 mg (27 μmol) of azobis(isobutyronitrile) were added to the reaction solution obtained as described above, and after argon bubbling was carried out for 10 minutes, reaction was carried out for 40 hours at 65° C. After reaction, a part of the reaction solution was collected and measured by $^1$H-NMR. As a result, it was confirmed that 98% of the charged amount of the n-butyl methacrylate had polymerized, whereby a partial block copolymer in which an n-butyl methacrylate polymer (polymer block (C)) bonded with the polymer block (B) was produced.

[Block Copolymer Production]

Production was performed by the same method as in the section [Block Copolymer Production] of Example 13, except that the reaction solution obtained as described above was used and 10 mL of 1,4-dioxane, 3.30 g (29.2 mmol) of N-isopropylacrylamide, and 4.4 mg (27 μmol) of azobis(isobutyronitrile) were added thereto. After reaction, a part of the reaction solution was collected and measured by $^1$H-NMR. As a result, it was confirmed that 99% of the charged amount of the N-isopropylacrylamide had polymerized. The obtained reaction solution was treated by the same method as in the section [Block Copolymer Production] of Example 13, whereby 3.5 g of a block copolymer comprising the 2-methoxyethyl acrylate polymer block (B), the n-butyl methacrylate polymer block (C), and an N-isopropylacrylamide polymer block (A) was obtained. The composition, Mn, and Mw/Mn of the obtained block copolymer are shown in Table 2.

[Surface Treatment Agent Preparation]

Preparation was performed by the same method as in the section [Surface Treatment Agent Preparation] of Example 13, except that the above block copolymer was used, to prepare a 0.1 wt % surface treatment agent.

[Membrane Evaluation]

Preparation was performed by the same method as described in the section [Membrane Evaluation] of Example 13, except that the above surface treatment agent was used, to prepare a cell culture substrate having a membrane formed from the block copolymer comprising the 2-methoxyethyl acrylate polymer block (B), the n-butyl methacrylate polymer block (C), and the N-isopropylacrylamide polymer block (A) introduced onto the surface thereof. The membrane thickness was 11 nm. The water contact angles at 40° C. and 20° C. are shown in Table 2. The water contact angle at 20° C. was lower than the water contact angle at 40° C. and was less than 40°, indicating high hydrophilicity.

[Cell Culture Evaluation and Separation Evaluation]

Evaluation was performed by the same method as in the section [Cell Culture Evaluation and Separation Evaluation] of Example 13, except that the cell culture substrate prepared as described above was used. Cell proliferation was confirmed, and after culturing was carried out until the cultured cells covered 100% of the substrate, the number of cells was confirmed with a 10×10 magnification microscope. By cooling for 15 minutes, 100% of the cells detached in a sheet form.

Example 17

[Production of Polymer Block (B)]

0.70 g (5.4 mmol) of 2-methoxyethyl acrylate, 1.15 g (8.1 mmol) of n-butyl methacrylate, 55 mg (135 μmol) of 4-cyano-4-[(dodecylsulfonylthiocarbonyl) sulfonyl] pentanoic acid as a RAFT agent, and 4.4 mg (27 μmol) of azobis(isobutyronitrile) as an initiator were added to a 100 mL test tube having a three-way valve, and were dissolved in 5 mL of 1,4-dioxane. After argon bubbling was carried out for 10 minutes, reaction was carried out for 40 hours at 65° C. After reaction, a part of the reaction solution was collected and measured by $^1$H-NMR. As a result, it was confirmed that 99% of the charged amount of the 2-methoxyethyl acrylate and 98% of the charged amount of the n-butyl methacrylate had polymerized, whereby a copolymer of 2-methoxyethyl acrylate and n-butyl methacrylate (2-methoxyethyl acrylate: 40.3 mol % and n-butyl methacrylate: 59.7 mol %) (copolymer block (B) was produced. The HLB value of the obtained polymer block (B) is 9.1.

[Partial Block Copolymer Production]

15 mL of 1,4-dioxane, 1.61 g (11.3 mmol) of n-butyl methacrylate, and 4.4 mg (27 μmol) of azobis(isobutyronitrile) were added to the reaction solution obtained as described above, and after argon bubbling was carried out for 10 minutes, reaction was carried out for 40 hours at 65° C. After reaction, a part of the reaction solution was collected and measured by $^1$H-NMR. As a result, it was confirmed that 98% of the charged amount of the n-butyl methacrylate had polymerized, whereby a partial block copolymer in which an n-butyl methacrylate polymer (polymer block (C)) bonded with the copolymer block (B) was produced.

[Block Copolymer Production]

Production was performed by the same method as in the section [Block Copolymer Production] of Example 16, except that the reaction solution obtained as described above was used. After reaction, a part of the reaction solution was collected and measured by $^1$H-NMR. As a result, it was confirmed that 99% of the charged amount of the N-isopropylacrylamide had polymerized. The obtained reaction solution was treated by the same method as in the section [Block Copolymer Production] of Example 13, whereby 3.5 g of a block copolymer comprising the copolymer block (B) of 2-methoxyethyl acrylate and n-butyl methacrylate, the n-butyl methacrylate polymer block (C), and an N-isopropylacrylamide polymer block (A) was obtained as a white powder. The composition. Mn, and Mw/Mn of the obtained block copolymer are shown in Table 2.

[Surface Treatment Agent Preparation]

Preparation was performed by the same method as in the section [Surface Treatment Agent Preparation] of Example 13, except that the above block copolymer was used, to prepare a 0.1 wt % surface treatment agent.

[Membrane Evaluation]

Preparation was performed by the same method as described in the section [Membrane Evaluation] of Example 13, except that the above surface treatment agent was used, to prepare a cell culture substrate having a membrane formed from the block copolymer comprising the copolymer block (B) of 2-methoxyethyl acrylate and n-butyl methacrylate, the n-butyl methacrylate polymer block (C), and the N-isopropylacrylamide polymer block (A) introduced onto the surface thereof. The membrane thickness was 11 nm. The water contact angles at 40° C. and 20° C. are shown in Table 2. The water contact angle at 20° C. was lower than the water contact angle at 40° C. and was less than 40°, indicating high hydrophilicity.

[Cell Culture Evaluation and Separation Evaluation]

Evaluation was performed by the same method as in the section [Cell Culture Evaluation and Separation Evaluation] of Example 13, except that the cell culture substrate prepared as described above was used. Cell proliferation was confirmed, and after culturing was carried out until the cultured cells covered 100% of the substrate, the number of cells was confirmed with a 10×10 magnification microscope. By cooling for 15 minutes, 100% of the cells had detached in a sheet form.

Example 18

[Production of Polymer Block (C)]

3.7 g (25.8 mmol) of n-butyl methacrylate, 108 mg (267 μmol) of 4-cyano-4-[(dodecylsulfonylthiocarbonyl) sulfonyl] pentanoic acid as a RAFT agent, and 8.8 mg (53 μmol) of azobis(isobutyronitrile) as an initiator were added to a 100 mL test tube having a three-way valve, and were dissolved in 10 mL of 1,4-dioxane. After argon bubbling was carried out for 10 minutes, reaction was carried out for 30 hours at 65° C. After reaction, a part of the reaction solution was collected and measured by $^1$H-NMR. As a result, it was confirmed that 95% of the charged amount of the n-butyl methacrylate had polymerized, whereby a polymer of n-butyl methacrylate (polymer block (C)) was produced.

[Partial Block Copolymer Production]

10 mL of 1,4-dioxane, 2.7 g (17.2 mmol) of 2-dimethylaminoethyl methacrylate, and 8.8 mg (53 μmol) of azobis(isobutyronitrile) were added to the reaction solution obtained as described above, and after argon bubbling was carried out for 10 minutes, reaction was carried out for 30 hours at 65° C. After reaction, a part of the reaction solution was collected and measured by $^1$H-NMR. As a result, it was confirmed that 96% of the charged amount of the 2-dimethylaminoethyl methacrylate had polymerized, whereby a partial block copolymer comprising the n-butyl methacrylate polymer block (C) and a 2-dimethylaminoethyl methacrylate polymer block (B) was produced.

[Block Copolymer Synthesis]

20 mL of 1,4-dioxane, 4.8 g (42.4 mmol) of N-isopropylacrylamide, and 8.8 mg (53 μmol) of azobis(isobutyronitrile) were added to the reaction solution obtained as described above, and after argon bubbling was carried out for 10 minutes, reaction was carried out for 45 hours at 65° C. After reaction, a part of the reaction solution was collected and measured by $^1$H-NMR As a result, it was confirmed that 99% of the charged amount of the N-isopropylacrylamide had polymerized. The reaction solution was poured into 300 mL of distilled water, and a precipitated white solid was filtered. The obtained white solid was dissolved in 300 mL of chloroform, 5 g of anhydrous magnesium sulfate was added to the obtained solution, and the mixture was stirred at room temperature for 30 minutes. The resulting suspension was filtered to remove the magnesium sulfate, and the chloroform was distilled off from the filtrate under reduced pressure using an evaporator to concentrate to 30 mL. The obtained concentrated solution was poured into 300 mL of hexane, and the precipitated white solid was filtered. The obtained white solid was dried under reduced pressure at 80° C. for 6 hours to obtain 6.0 g of a block copolymer comprising the n-butyl methacrylate polymer block (C), the 2-dimethylaminoethyl methacrylate polymer block (B), and an N-isopropylacrylamide polymer block (A) as a white powder. The composition, Mn, and Mw/Mn of the obtained block copolymer are shown in Table 2.

[Surface Treatment Agent Preparation]

Preparation was performed by the same method as in the section [Surface Treatment Agent Preparation] of Example 13, except that the above block copolymer was used, to prepare a 0.1 wt % surface treatment agent.

[Membrane Evaluation]

Preparation was performed by the same method as described in the section [Membrane Evaluation] of Example 13, except that the above surface treatment agent was used, to prepare a cell culture substrate having a membrane formed from the block copolymer comprising the n-butyl methacrylate polymer block (C), the 2-dimethylaminoethyl methacrylate polymer block (B), and the N-isopropylacrylamide polymer block (A) introduced onto the surface thereof. The membrane thickness was 10 nm. The water contact angles at 40° C. and 20° C. are shown in Table 2. The water contact angle at 20° C. was lower than the water contact angle at 40° C. and was less than 40°, indicating high hydrophilicity.

[Cell Culture Evaluation and Separation Evaluation]

Evaluation was performed by the same method as in the section [Cell Culture Evaluation and Separation Evaluation] of Example 13, except that the cell culture substrate prepared as described above was used. Cell proliferation was confirmed, and after culturing was carried out until the cultured cells covered 100% of the substrate, the number of cells was confirmed with a 10×10 magnification microscope. After the substrate was cooled to 10° C., the detached cells were removed with an aspirator, and the number of cells was again confirmed with a 10×10 magnification microscope. By cooling for 15 minutes, 100% of the cells had detached in a sheet form.

Comparative Example 5

[Cell Culture Evaluation and Separation Evaluation]

Evaluation was performed by the same method as in the section [Cell Culture Evaluation and Separation Evaluation] of Example 10, except that the cell culture substrate having a partial block copolymer comprising an n-butyl methacrylate polymer block (C) and an N-isopropylacrylamide polymer block (A) introduced onto the surface thereof prepared in the section [Membrane Evaluation] of Comparative Example 2 was used. Cell proliferation was confirmed, and after culturing was carried out until the cultured cells covered 100% of the substrate, the number of cells was confirmed with a 10×10 magnification microscope. After the substrate was cooled to 10° C., the detached cells were removed with an aspirator, and the number of cells was again confirmed with a 10×10 magnification microscope. Even after cooling for 1 hour, the cells did not detached.

Comparative Example 6

[Cell Culture Evaluation and Separation Evaluation]

Evaluation was performed by the same method as in the section [Cell Culture Evaluation and Separation Evaluation] of Example 12, except that the cell culture substrate having a partial block copolymer comprising an n-butyl methacrylate polymer block (C) and an N-isopropylacrylamide polymer block (A) introduced onto the surface thereof prepared in the section [Membrane Evaluation] of Comparative Example 2 was used. Cell proliferation was confirmed, and after culturing was carried out until the cultured cells covered 100% of the substrate, the number of cells was confirmed with a 10×10 magnification microscope. After the substrate was cooled to 10° C., the detached cells were removed with an aspirator, and the number of cells was again confirmed with a 10×10 magnification microscope. Even after cooling for 1 hour, the cells did not detached.

Comparative Example 7

[Cell Culture Evaluation and Separation Evaluation]
Evaluation was performed by the same method as in the section [Cell Culture Evaluation and Separation Evaluation] of Example 12, except that a 35 mm φ UpCell® dish manufactured by Cell Seed Co., Ltd., was used. Cell proliferation was confirmed, and after culturing was carried out until the cultured cells covered 100% of the substrate, the number of cells was confirmed with a 10×10 magnification microscope. After the substrate was cooled to 10° C., the detached cells were removed with an aspirator, and the number of cells was again confirmed with a 10×10 magnification microscope. Even after cooling for 1 hour, the cells did not detached.

Comparative Example 8

Evaluation was performed by the same method as in the section [Cell Culture Evaluation and Separation Evaluation] of Example 10, except that a cell culture treated 35 mm φ dish manufactured by Corning Inc., was used. Cell proliferation was confirmed, and after culturing was carried out until the cultured cells covered 100% of the substrate, the number of cells was confirmed with a 10×10 magnification microscope. After the substrate was cooled to 10° C., the detached cells were removed with an aspirator, and the number of cells was again confirmed with a 10×10 magnification microscope. Even after cooling for 1 hour, the cells did not detached.

Comparative Example 9

[Membrane Evaluation]
The water contact angles at 40° C. and 20° C. of an IWAKI 100 mm φ dish for tissue culture are shown in Table 3. The water contact angles at 40° C. and 20° C. were the same angle (57°) and the dish exhibited no temperature-responsiveness.
[Cell Culture Evaluation and Separation Evaluation]
Evaluation was performed by the same method as in the section [Cell Culture Evaluation and Separation Evaluation] of Example 12, except that the above IWAKI dish for tissue culture (Φ 9 cm) was used. Cell proliferation was confirmed, and after culturing was carried out until the cultured cells covered 100% of the substrate, the number of cells was confirmed with a 10×10 magnification microscope. After the substrate was cooled to 10° C., the detached cells were removed with an aspirator, and the number of cells was again confirmed with a 10×10 magnification microscope. Even after cooling for 1 hour, the cells did not detached.

Comparative Example 10

[Polymer Block Production]
1.00 g (3.39 mmol) of 2-methacryloyloxyethyl phosphorylcholine, 1.12 g (7.88 mmol) of n-butyl methacrylate, 24 mg (59 μmol) of 4-cyano-4-[(dodecylsulfonylthiocarbonyl)sulfonyl]pentanoic acid, and 1 mg (6 μmol) of azobis (isobutyronitrile) were added to a test tube, and were dissolved in 20 mL of a 1:1 mixed solution of 1,4-dioxane/ethanol. After nitrogen bubbling was carried out for 15 minutes, reaction was carried out for 18 hours at 65° C. After reaction, the reaction solution was poured into 500 mL of diethyl ether, and a precipitated white solid was filtered and dried to obtain a copolymer block of 2-methacryloyloxyethyl phosphorylcholine and n-butyl methacrylate.
[Block Copolymer Production]
1.00 g of the above copolymer block, 1.20 g (10.6 mmol) of N-isopropylacrylamide, and 6 mg (37 μmol) of azobis (isobutyronitrile) were added to a test tube, and were dissolved in 20 mL of a 1:1 mixed solution of 1,4-dioxane/ethanol. After nitrogen bubbling was carried out for 15 minutes, reaction was carried out for 18 hours at 65° C. After reaction, the reaction solution was poured into 500 mL of diethyl ether, and a precipitated white solid was filtered and dried to obtain a block copolymer comprising the copolymer block of 2-methacryloyloxyethyl phosphorylcholine and n-butyl methacrylate and an N-isopropylacrylamide polymer block. The ratios of the repeating units of the obtained block copolymer were 12 mol % of the repeating units generated by polymerizing 2-methacryloyloxyethyl phosphorylcholine, 25 mol % of the repeating units generated by polymerizing n-butyl methacrylate, and 63 mol %/o of the repeating units generated by polymerizing N-isopropylacrylamide. These ratios were substantially the same as the block copolymer synthesized in Example 1. The Mn and Mw/Mn of the obtained block copolymer are shown in Table 3.
[Surface Treatment Agent Preparation]
Preparation was performed by the same method as in the section [Surface Treatment Agent Preparation] of Example 1, except that the above block copolymer was used, to prepare a surface treatment agent.
[Membrane Evaluation]
Preparation of a cell culture substrate was performed by the same method as described in the section [Membrane Evaluation] of Example 1, except that the above surface treatment agent was used, to prepare a cell culture substrate having a membrane formed from the block copolymer comprising the copolymer block of 2-methacryloyloxyethyl phosphorylcholine and n-butyl methacrylate and the N-isopropylacrylamide polymer block introduced onto the surface thereof. The membrane thickness was 100 nm. The water contact angles at 40° C. and 20° C. are shown in Table 3. Though the water contact angle at 20° C. was lower than the water contact angle at 40° C. and the substrate exhibited temperature-responsiveness, the water contact angle at 20° C. was 40° or more.
[Cell Culture Evaluation and Separation Evaluation]
Evaluation was performed in the same manner as in the section [Cell Culture Evaluation and Separation Evaluation] of Example 1, except that the cell culture substrate having a membrane formed from the block copolymer comprising the copolymer block of 2-methacryloyloxyethyl phosphorylcholine and n-butyl methacrylate and an N-isopropylacrylamide polymer block introduced onto the surface thereof prepared as described above was used, Chinese hamster ovary-derived CHO cells (100 cells/mm$^2$) were used in place of murine connective tissue L929 cells (100 cells/mm$^2$), and 10 vol % of FBS/Ham's F-12 was used as the culture solution in place of the 10 vol % FBS/DMEM, and cell proliferation was confirmed. Furthermore, after culturing until the cultured cells covered 100% of the substrate, by cooling the substrate to 10° C., 10% of the cells were detached after 15 minutes.

Comparative Example 1

[Copolymer Production]

1.00 g (3.39 mmol) of 2-methacryloyloxyethyl phosphorylcholine. 1.12 g (7.88 mmol) of n-butyl methacrylate. 2.00 g (17.7 mmol) of N-isopropylacrylamide. 24 mg (59 µmol) of 4-cyano-4-[(dodecylsulfonylthiocarbonyl) sulfonyl] pentanoic acid, and 1.9 mg (12 µmol) of azobis(isobutyronitrile) were added to a test tube, and were dissolved in 40 mL of a 1:1 mixed solution of 1,4-dioxane/ethanol. After nitrogen bubbling was carried out for 15 minutes, reaction was carried out for 18 hours at 65° C. After reaction, the reaction solution was poured into 500 mL of diethyl ether, and a precipitated white solid was filtered and dried to obtain a copolymer of 2-methacryloyloxyethyl phosphorylcholine, n-butyl methacrylate, and N-isopropylacrylamide. The ratios of the repeating units of the obtained copolymer were 11 mol % of the repeating units generated by polymerizing 2-methacryloyloxyethyl phosphorylcholine, 26 mol % of the repeating units generated by polymerizing n-butyl methacrylate, and 63 mol % of the repeating units generated by polymerizing N-isopropylacrylamide. These ratios were substantially the same as the block copolymer produced in Example 1. The Mn and Mw/Mn of the obtained block copolymer are shown in Table 3.

[Surface Treatment Agent Preparation]

Preparation was performed by the same method as described in the section [Surface Treatment Agent Preparation] of Example 1, except that the above copolymer was used, to prepare a surface treatment agent.

[Membrane Evaluation]

Preparation of a cell culture substrate was performed by the same method as the method described in the section [Membrane Evaluation] of Example 1, except that the above surface treatment agent was used, to prepare a cell culture substrate having a membrane formed from the copolymer of 2-methacryloyloxyethyl phosphorylcholine, n-butyl methacrylate, and N-isopropylacrylamide introduced onto the surface thereof. The water contact angles at 40° C. and 20° C. are shown in Table 3. The water contact angles at 40° C. and 20° C. were the same angle, and the substrate did not exhibit temperature-responsiveness.

[Cell Culture Evaluation and Separation Evaluation]

Evaluation was performed in the same manner as in the section [Cell Culture Evaluation and Separation Evaluation] of Example 1, except that the cell culture substrate having a membrane formed from the copolymer of 2-methacryloyloxyethyl phosphorylcholine, n-butyl methacrylate, and N-isopropylacrylamide introduced onto the surface thereof prepared as described above was used, Chinese hamster ovary-derived CHO cells (100 cells/mm$^2$) were used in place of murine connective tissue L929 cells (100 cells/mm$^2$), and 10 vol % of FBS/Ham's F-12 was used as the culture solution in place of the 10 vol % FBS/DMEM, and cell proliferation was confirmed. Furthermore, after culturing until the cultured cells covered 100% of the substrate, even though the substrate was cooled to 10° C., none of the cells had detached at all even after 15 minutes had elapsed.

Comparative Example 12

Evaluation was performed in the same manner as in the section [Cell Culture Evaluation and Separation Evaluation] of Example 1, except that the cell culture treated 35 mm φ dish manufactured by Corning Inc., evaluated in the section [Membrane Evaluation] of Comparative Example 4 was used, Chinese hamster ovary-derived CHO cells (100 cells/mm$^2$) were used in place of murine connective tissue L929 cells (100 cells/mm$^2$), and 10 vol % of FBS/Ham's F-12 was used as the culture solution in place of the 10 vol % FBS/DMEM, and cell proliferation was confirmed. Furthermore, after culturing until the cultured cells covered 100% of the substrate, though the substrate was cooled to 10° C., none of the cells had detached even after 15 minutes had elapsed.

Comparative Example 13

Evaluation was performed in the same manner as in the section [Cell Culture Evaluation and Separation Evaluation] of Example 13, except that the IWAKI 100 mm φ dish for tissue culture evaluated in the section [Membrane Evaluation] of Comparative Example 9 was used, and cell proliferation was confirmed. Furthermore, after culturing until the cultured cells covered 100% of the substrate, though the substrate was cooled to 10° C., none of the cells had detached even after 15 minutes had elapsed.

Comparative Example 14

[Partial Block Copolymer Production]

20 mL of 1,4-dioxane, 4.8 g (42.4 mmol) of N-isopropylacrylamide, and 8.8 mg (53 µmol) of azobis(isobutyronitrile) were added to the reaction solution obtained in the section [Production of Polymer Block (B)] of Example 10, and after argon bubbling was carried out for 10 minutes, reaction was carried out for 45 hours at 65° C. After reaction, a part of the reaction solution was collected and measured by $^1$H-NMR. As a result, it was confirmed that 98% of the charged amount of the N-isopropylacrylamide had polymerized. The reaction solution was poured into 300 mL of distilled water and a precipitated white solid was filtered. The obtained white solid was dissolved in 300 mL of chloroform, 5 g of anhydrous magnesium sulfate was added to the obtained solution, and the mixture was stirred at room temperature for 30 minutes. The resulting suspension was filtered to remove the magnesium sulfate, and the chloroform was distilled off from the filtrate under reduced pressure using an evaporator to concentrate to 30 mL. The obtained concentrated solution was poured into 300 mL of hexane, and the precipitated white solid was filtered. The obtained white solid was dried under reduced pressure at 80° C. for 6 hours to obtain 5.8 g of a block copolymer comprising a 2-dimethylaminoethyl methacrylate polymer block (B), and an N-isopropylacrylamide polymer block (A) as a white powder. The composition, Mn, and Mw/Mn of the obtained block copolymer are shown in Table 3.

[Surface Treatment Agent Preparation]

Preparation was performed by the same method as in the section [Surface Treatment Agent Preparation] of Example 10, except that the above partial block copolymer was used, to prepare a 0.5 wt % surface treatment agent.

[Membrane Evaluation]

Preparation of a cell culture substrate was performed by the method described in the section [Membrane Evaluation] of Example 10, except that the above surface treatment agent was used. The membrane thickness was 10 nm. The water contact angles at 40° C. and 20° C. are shown in Table 3. The water contact angles at 40° C. and 20° C. were the same angle (57°), and the substrate did not exhibit temperature-responsiveness, which was equivalent to the IWAKI 100 mm φ dish for tissue culture evaluated in the section

[Membrane Evaluation] of Comparative Example 9, and accordingly, it was discovered that the block copolymer eluted in water.

The types, composition ratios of each of the blocks, Mn, Mw/Mn, and water contact angles of the block copolymers produced in the Examples and Comparative Examples described above are shown in Tables 1 to 3. Furthermore, the results of the cell culture evaluations of the Examples, Reference Examples, and Comparative Examples described above are shown in Tables 4 to 8. Note that, regarding the cultured cells in Tables 4 to 8. A indicates L929 cells, B indicates CHO cells, C indicates human bone marrow-derived mesenchymal stem cells, D indicates human progenitor fat cells, and E indicates human fetal lung-derived normal diploid fibroblast cells.

TABLE 1

| Example, Comparative Example | Block (A) | LCST (°C.) | Block (B) | HLB Value | Block (C) | HLB Value | Composition (%) (a) | (b) | (c) | Mn | Mw/Mn | Water Contact Angle (°) 40°C. | 20°C. |
|---|---|---|---|---|---|---|---|---|---|---|---|---|---|
| Example 1 | N-isopropyl-acrylamide polymer | 32 | 2-methacryloyloxyethyl phosphorylcholine polymer | 14 | n-butyl methacrylate-polymer | 6 | 59 | 14 | 27 | $11.0 \times 10^4$ | 1.5 | 21 | 14 |
| Example 3 | N-isopropyl-acrylamide polymer | 32 | 2-methacryloyloxyethyl phosphorylcholine polymer | 14 | n-butyl methacrylate-polymer | 6 | 62 | 7 | 31 | $12.3 \times 10^4$ | 1.6 | 36 | 24 |
| Example 5 | N-isopropyl-acrylamide polymer | 32 | polyethylene glycol methacrylate polymer | 16 | n-butyl methacrylate-polymer | 6 | 61 | 17 | 22 | $3.4 \times 10^4$ | 1.5 | 41 | 36 |
| Example 6 | N-isopropyl-acrylamide polymer | 32 | 2-dimethylaminoethyl methacrylate polymer | 11 | n-butyl methacrylate-polymer | 6 | 59 | 20 | 21 | $3.1 \times 10^4$ | 1.4 | 42 | 36 |
| Example 7 | N-isopropyl-acrylamide polymer | 32 | 2-methoxyethyl acrylate polymer | 14 | n-butyl methacrylate-polymer | 6 | 55 | 25 | 20 | $2.7 \times 10^4$ | 1.4 | 44 | 38 |
| Example 8 | 2-ethoxyethylvinyl ether polymer | 20 | dimethyl (3-methacryloyl-aminopropyl) (3-sulfonatopropyl) aminium polymer | 11 | styrene polymer | 0 | 59 | 10 | 31 | $6.1 \times 10^4$ | 1.6 | 46 | 38 |
| Example 9 | methyl vinyl ether polymer | 34 | dimethyl (3-methacryloyl-aminopropyl) (3-sulfonatopropyl) aminium polymer | 11 | styrene polymer | 0 | 61 | 10 | 29 | $5.7 \times 10^4$ | 1.5 | 46 | 38 |
| Comparative Example 1 | 35 mm φ UpCell ® dish manufactured by CellSeed Co., Ltd | | | | | | — | — | — | — | — | 52 | 48 |
| Comparative Example 2 | N-isopropyl-acrylamide polymer | 32 | — | | n-butyl methacrylate-polymer | 6 | 50 | 0 | 50 | $1.2 \times 10^4$ | 1.5 | 74 | 60 |
| Comparative Example 3 | N-isopropyl-acrylamide polymer | 32 | — | | n-butyl methacrylate-polymer | 6 | 73 | 0 | 27 | $2.1 \times 10^4$ | 1.2 | 56 | 43 |
| Comparative Example 4 | Cell culture treated 35 mm φ dish manufactured by Corning Inc. | | | | | | — | — | — | — | — | 48 | 48 |

TABLE 2

| Example, Comparative Example | Block (A) LCST (° C.) | | Block (B) HLB Value | | Block (C) HLB Value | Composition (%) | | | Mn | Mw/Mn | Water Contact Angle (°) | |
|---|---|---|---|---|---|---|---|---|---|---|---|---|
| | | | | | | (a) | (b) | (c) | | | 40° C. | 20° C. |
| Example 10 | N-isopropyl-acrylamide polymer | 32 | 2-dimethyl-aminoethyl methacrylate polymer | 11 | n-butyl methacrylate polymer | 6 | 56 | 22 | 22 | $5.7 \times 10^4$ | 1.3 | 50 | 38 |
| Example 11 | N-isopropyl-acrylamide polymer | 32 | 2-dimethyl-aminoethyl methacrylate polymer | 11 | n-butyl methacrylate polymer | 6 | 49 | 8 | 43 | $14.8 \times 10^4$ | 1.5 | 46 | 32 |
| Example 13 | N-isopropyl-acrylamide polymer | 32 | 2-dimethyl-aminoethyl methacrylate/ n-butyl methacrylate copolymer | 9 | dimethyl amino-ethyl methacrylate/ n-butyl methacrylate copolymer | 7 | 50 | 5 | 45 | $5.0 \times 10^4$ | 1.3 | 55 | 38 |
| Example 14 | N-isopropyl-acrylamide polymer | 32 | 2-dimethyl-aminoethyl methacrylate/ n-butyl methacrylate copolymer | 9 | n-butyl methacrylate polymer | 6 | 50 | 20 | 30 | $5.2 \times 10^4$ | 1.2 | 53 | 38 |
| Example 15 | N-isopropyl-acrylamide polymer | 32 | 2-dimethyl-aminoethyl methacrylate/ methyl methacrylate copolymer | 10 | n-butyl methacrylate polymer | 6 | 51 | 27 | 22 | $5.3 \times 10^4$ | 1.3 | 54 | 39 |
| Example 16 | N-isopropyl-acrylamide polymer | 32 | 2-methoxyethyl acrylate polymer | 14 | n-butyl methacrylate polymer | 6 | 54 | 10 | 36 | $5.0 \times 10^4$ | 1.3 | 44 | 37 |
| Example 17 | N-isopropyl-acrylamide polymer | 32 | 2-methoxyethyl acrylate/ n-butyl methacrylate copolymer | 9 | n-butyl methacrylate polymer | 6 | 54 | 25 | 21 | $5.1 \times 10^4$ | 1.2 | 53 | 38 |
| Example 18 | N-isopropyl-acrylamide polymer | 32 | 2-dimethyl-aminoethyl methacrylate polymer | 11 | n-butyl methacrylate polymer | 6 | 50 | 20 | 30 | $5.0 \times 10^4$ | 1.5 | 50 | 39 |

TABLE 3

| Example, Comparative Example | Block (A) LCST (° C.) | | Block (B) HLB Value | Block (C) HLB Value | Composition (%) | | | Mn | Mw/Mn | Water Contact Angle (°) | |
|---|---|---|---|---|---|---|---|---|---|---|---|
| | | | | | (a) | (b) | (c) | | | 40° C. | 20° C. |
| Comparative Example 9 | IWAKI 100 mm φ dish for tissue culture | | | | — | — | — | — | — | 57 | 57 |
| Comparative Example 10 | N-isopropyl-acrylamide polymer | 32 | 2-methacryloyloxyethyl phosphorylcholine/ n-butyl methacrylate copolymer | | — | — | — | $11.5 \times 10^4$ | 1.3 | 52 | 42 |
| Comparative Example 11 | 2 methacryloyloxyethyl phosphorylcholine/ n-butyl methacrylate/ N-isopropylacrylamide copolymer | | | | — | — | — | $10.5 \times 10^4$ | 1.4 | 48 | 48 |
| Comparative Example 14 | N-isopropyl-acrylamide polymer | 32 | 2-dimethyl-aminoethyl methacrylate polymer | 11 | — | 72 | 28 | 0 | $4.5 \times 10^4$ | 1.3 | 57 | 57 |

TABLE 4

| Example, Ref Example, Comp. Example | Block (A) | LCST (° C.) | Block (B) | HLB Value | Block (C) | HLB Value | Cell Type | Cell Proliferation | Cell Separability (%) |
|---|---|---|---|---|---|---|---|---|---|
| Example 1 | N-isopropyl-acrylamide polymer | 32 | 2-methacryloyloxyethyl phosphorylcholine polymer | 14 | n-butyl methacrylate polymer | 6 | A | Y | 100 |
| Reference Example 1 | — | — | 2-methacryloyloxyethyl phosphorylcholine polymer | 14 | n-butyl methacrylate polymer | 6 | A | N | N/A |
| Example 3 | N-isopropyl-acrylamide polymer | 32 | 2-methacryloyloxyethyl phosphorylcholine polymer | 14 | n-butyl methacrylate polymer | 6 | A | Y | 100 |
| Reference Example 3 | — | — | 2-methacryloyloxyethyl phosphorylcholine polymer | 14 | n-butyl methacrylate polymer | 6 | A | N | N/A |
| Example 5 | N-isopropyl-acrylamide polymer | 32 | polyethylene glycol methacrylate polymer | 16 | n-butyl methacrylate polymer | 6 | A | Y | 100 |
| Example 6 | N-isopropyl-acrylamide polymer | 32 | 2-dimethylaminoethyl methacrylate polymer | 11 | n-butyl methacrylate polymer | 6 | A | Y | 100 |
| Example 7 | N-isopropyl-acrylamide polymer | 32 | 2-methoxyethyl acrylate polymer | 14 | n-butyl methacrylate polymer | 6 | A | Y | 80 |
| Example 8 | 2-ethoxyethylvinyl ether polymer | 20 | dimethyl(3-methacryloylaminopropyl)(3-sulfonato-propyl)aminium polymer | 11 | styrene polymer | 0 | A | Y | 72 |
| Example 9 | methyl vinyl ether polymer | 34 | dimethyl(3-methacryloylaminopropyl)(3-sulfonato-propyl)aminium polymer | 11 | styrene polymer | 0 | A | Y | 73 |
| Comparative Example 1 | 35 mm φ UpCell ® dish manufactured by CellSeed Co., Ltd. | | | | | | A | Y | 65 |
| Comparative Example 2 | N-isopropyl-acrylamide polymer | 32 | — | — | n-butyl methactrate polymer | 6 | A | Y | 60 |
| Comparative Example 3 | N-isopropyl-acrylamide polymer | 32 | — | — | n-butyl methactrate polymer | 6 | A | Y | 63 |
| Comparative Example 4 | Cell Culture treated 35 mm φ dish manufactured by Corning Inc. | | | | | | A | Y | 0 |

TABLE 5

| Example, Ref. Example, Comp. Example | Block (A) | LCST (° C.) | Block (B) | HLB Value | Block (C) | HLB Value | Cell Type | Cell Proliferation | Cell Separability (%) |
|---|---|---|---|---|---|---|---|---|---|
| Example 2 | N-isopropyl-acrylamide polymer | 32 | 2-methacryloyloxyethyl phosphorylcholine polymer | 14 | n-butyl methacrylate polymer | 6 | B | Y | 70 |
| Example 2 | — | — | 2-methacryloyloxyethyl phosphorylcholine polymer | 14 | n-butyl methacrylate polymer | 6 | B | N | N/A |
| Example 4 | N-isopropyl-acrylamide polymer | 32 | 2-methacryloyloxyethyl phosphorylcholine polymer | 14 | n-butyl methacrylate polymer | 6 | B | Y | 70 |
| Reference Example 4 | — | — | 2-methacryloyloxyethyl phosphorylcholine polymer | 14 | n-butyl methacrylate polymer | 6 | B | N | N/A |
| Comparative Example 10 | N-isopropyl-acrylamide polymer | 32 | 2-methacryloyloxyethyl phosphorylcholine/n-butyl methacrylate copolymer | | | | B | Y | 10 |
| Comparative Example 11 | 2-methacryloyloxyethyl phosphorylcholine/n-butyl methacrylate/N-isopropylacrylamide copolymer | | | | | | B | Y | 0 |
| Comparative Example 12 | Cell culture treated 35 mm φ dish manufactured by Corning Inc. | | | | | | B | Y | 0 |

TABLE 6

| Example, Ref. Example, Comp. Example | Block (A) | LCST (° C.) | Block (B) | HLB Value | Block (C) | HLB Value | Cell Type | Cell Proliferation | Cell Separability (%) |
|---|---|---|---|---|---|---|---|---|---|
| Example 10 | N-isopropyl-acrylamide polymer | 32 | 2-dimethylaminoethyl methacrylate polymer | 11 | n-butyl methacrylate polymer | 6 | C | Y | 100 |
| Example 11 | N-isopropyl-acrylamide polymer | 32 | 2-dimethylaminoethyl methacrylate polymer | 11 | n-butyl methacrylate polymer | 6 | C | Y | 100 |
| Comparative Example 5 | N-isopropyl-acrylamide polymer | 32 | — | — | n-butyl methacrylate polymer | 6 | C | Y | 0 |
| Comparative Example 8 | Cell culture treated 35 mm φ dish manufactured by Corning Inc. | | | | | | C | Y | 0 |

TABLE 7

| Example, Ref. Example, Comp. Example | Block (A) | LCST (° C.) | Block (B) | HLB Value | Block (C) | HLB Value | Cell Type | Cell Proliferation | Cell Separability (%) |
|---|---|---|---|---|---|---|---|---|---|
| Example 12 | N-isopropyl-acrylamide polymer | 32 | 2-dimethylaminoethyl methacrylate polymer | 11 | n-butyl methacrylate polymer | 6 | D | Y | 100 |
| Comparative Example 6 | N-isopropyl-acrylamide polymer | 32 | — | — | n-butyl methacrylate polymer | 6 | D | Y | 0 |
| | N-isopropyl-acrylamide polymer | 32 | — | — | n-butyl methacrylate polymer | 6 | C | Y | 0 |
| Comparative Example 7 | 35 mm φ UpCell ® dish manufactured by CellSeed Co., Ltd. | | | | | | D | Y | 0 |
| Comparative Example 9 | IWAKI 100 mm φ dish for tissue culture | | | | | | D | Y | 0 |

TABLE 8

| Example, Ref. Example, Comp. Example | Block (A) | LCST (° C.) | Block (B) | HLB Value | Block (C) | HLB Value | Cell Type | Cell Proliferation | Cell Separability (%) |
|---|---|---|---|---|---|---|---|---|---|
| Example 13 | N-isopropylacrylamide polymer | 32 | 2-dimethylaminoethyl methacrylate/n-butyl methacrylate copolymer | 9 | 2-dimethylaminoethyl methacrylate/n-butyl methacrylate copolymer | 7 | E | Y | 100 |
| Example 14 | N-isopropylacrylamide polymer | 32 | 2-dimethylaminoethyl methacrylate/n-butyl methacrylate copolymer | 9 | n-butyl methacrylate polymer | 6 | E | Y | 100 |
| Example 15 | N-isopropylacrylamide polymer | 32 | 2-dimethylaminoethyl methacrylate/n-butyl methacrylate copolymer | 10 | n-butyl methacrylate polymer | 6 | E | Y | 100 |
| Example 16 | N-isopropylacrylamide polymer | 32 | 2-methoxyethyl acrylate polymer | 14 | n-butyl methacrylate polymer | 6 | E | Y | 100 |
| Example 17 | N-isopropylacrylamide polymer | 32 | 2-methoxyethyl acrylate/n-butyl methacrylate copolymer | 9 | n-butyl methacrylate polymer | 6 | E | Y | 100 |

TABLE 8-continued

| Example, Ref. Example, Comp. Example | Block (A) | LCST (° C.) | Block (B) | HLB Value | Block (C) | HLB Value | Cell Type | Cell Proliferation | Cell Separability (%) |
|---|---|---|---|---|---|---|---|---|---|
| Example 18 | N-isopropyl-acrylamide polymer | 32 | 2-dimethyl-aminoethyl methacrylate | 11 | n-butyl methacrylate polymer | 6 | E | Y | 100 |
| Comparative Example 13 | | | IWAKI 100 mm φ dish for tissue culture | | | | E | Y | 0 |

Though the present invention has been described in detail and with reference to specific embodiments, it will be apparent to those skilled in the art that various changes and modifications can be made without departing from the gist and scope of the invention.

Note that the entire contents of the descriptions, claims, drawings, and abstracts of Japanese Patent Application No. 2016-152825 filed on Aug. 3, 2016 and Japanese Patent Application No. 2016-228031 filed on Nov. 24, 2016 are incorporated herein by way of reference as disclosure of the description of the present invention.

The invention claimed is:

1. A block copolymer comprising the following blocks (A), (B), and (C):

(A) a temperature-responsive polymer block having a lower critical solution temperature (LCST) in water in the range of 0° C. to 50° C.;

(B) a hydrophilic polymer block which does not have an LCST in the range of 0° C. to 50° C. and which has an HLB value (as determined by the Griffin method) in the range of 9 to 20, wherein the block (B) is a polymer comprising at least one repeating unit represented by the following Formula (5)

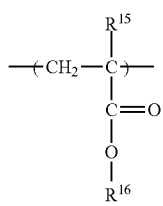

(5)

where $R^{15}$ is a hydrogen atom or methyl group and $R^{16}$ is $-(CH_2CH_2O)_i-(CH_2O)_j-(CH_2CH(CH_3)O)_k-R^{17}$ where $R^{17}$ is a hydrogen atom or $C_{1-10}$ alkyl group, i is an integer from 1 to 30, and j and k are each independently an integer from 0 to 30; and (C) a hydrophobic polymer block which does not have an LCST in the range of 0° C. to 50° C. and which has an HLB value as determined by the Griffin method in the range from 0 to less than 9, wherein the block (C) is a polymer comprising at least one repeating unit represented by the following Formula (11)

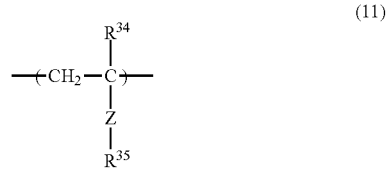

(11)

where $R^{34}$ is a hydrogen atom or methyl group, $R^{35}$ is a $C_{1-30}$ hydrocarbon group, and Z is an ester bond.

2. The block copolymer according to claim 1, wherein the block (A) is a polymer comprising at least one repeating unit selected from the group consisting of repeating units represented by the following Formula (1), repeating units represented by the following Formula (2), and repeating units represented by the following Formula (3):

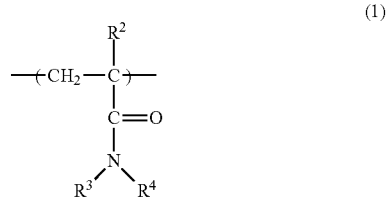

(1)

where $R^2$ is a hydrogen atom or methyl group, $R^3$ and $R^4$ are each independently a hydrogen atom, $C_{1-6}$ hydrocarbon group, $C_{2-4}$ hydrocarbon group which may be substituted with a $C_{1-2}$ alkyloxy group, $C_{2-4}$ hydrocarbon group which may be substituted with fluorine, furfuryl group, or tetrahydrofurfuryl group, and $R^3$ and $R^4$ may be connected to form a pyrrolidine ring, piperidine ring or morpholine ring;

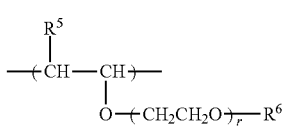

(2)

where $R^5$ is a hydrogen atom or methyl group, $R^6$ is a hydrogen atom or $C_{1-6}$ hydrocarbon group, and r is an integer from 1 to 10;

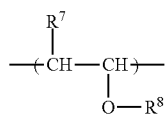
(3)

where $R^7$ is a hydrogen atom or methyl group and $R^8$ is a $C_{1-6}$ hydrocarbon group.

3. The block copolymer according to claim 1, wherein block (A), block (B), and block (C) constituting the block copolymer have the following mol % (a) to (c) with respect to the total thereof, respectively:
 (a) the ratio of block (A) is 25 mol % to 85 mol %;
 (b) the ratio of block (B) is 2 mol % to 50 mol %; and
 (c) the ratio of block (C) is 10 mol % to 70 mol %.

4. The block copolymer according to claim 1, wherein the number average molecular weight (Mn) of the block copolymer is in the range of 3,000 to 1,000,000.

5. The block copolymer according to claim 1, comprising at least one bond via a spacer between blocks (A), (B), and (C), wherein at least one of the bonds via the spacer is a divalent bond comprising at least one bond from among divalent bonds represented by the following Formulae (12) and (13):

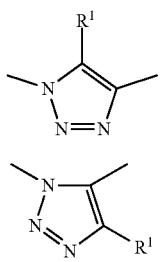

where $R^1$ is a hydrogen atom or $C_{1-20}$ hydrocarbon group.

6. A method for the production of the block copolymer according to claim 1, comprising the following (1) to (3):
 (1) producing any one of the blocks from among blocks (A), (B), and (C);
 (2) producing a partial block copolymer comprising the block produced in step (1) and, connected thereto, one of the blocks from among blocks (A), (B), and (C) except the block produced in step (1); and
 (3) producing a block copolymer comprising the partial block copolymer produced in step (2) and, connected thereto, the block among blocks (A), (B), and (C) which does not constitute a block copolymer comprising the partial block copolymer produced in step (2).

7. A surface treatment agent for substrates, comprising the block copolymer according to claim 1.

8. A membrane comprising the surface treatment agent according to claim 7 applied to a substrate.

9. A substrate for cell culture having a surface coated with the membrane according to claim 8.

10. A cell culture method, comprising culturing, using the cell culture substrate according to claim 9, a cell at a temperature higher than the LCST of the temperature-responsive polymer block, and after cell proliferation, lowering the temperature below the LCST to detach proliferated cells from the substrate.

11. The block copolymer according to claim 2, wherein block (A), block (B), and block (C) constituting the block copolymer have the following mol % (a) to (c) with respect to the total thereof, respectively:
 (a) the ratio of block (A) is 25 mol % to 85 mol %;
 (b) the ratio of block (B) is 2 mol % to 50 mol %; and
 (c) the ratio of block (C) is 10 mol % to 70 mol %.

12. The block copolymer according to claim 2, wherein the number average molecular weight (Mn) of the block copolymer is in the range of 3,000 to 1,000,000.

13. The block copolymer according to claim 1, wherein $R^{35}$ is selected from the group consisting of a methyl group, an ethyl group, a n-propyl group, an isopropyl group, a cyclopropyl group, a n-butyl group, a isobutyl group, a tert-butyl group, a n-hexyl group, an isohexyl group, a n-octyl group, a n-decyl group, a n-dodecyl group, a n-hexadecyl group, and a n-octadecyl group.

* * * * *

UNITED STATES PATENT AND TRADEMARK OFFICE
CERTIFICATE OF CORRECTION

PATENT NO. : 11,046,803 B2
APPLICATION NO. : 16/322361
DATED : June 29, 2021
INVENTOR(S) : Yukie Maejima et al.

It is certified that error appears in the above-identified patent and that said Letters Patent is hereby corrected as shown below:

On the Title Page

Item (56) other publications (Line 17), please change "Influence of thr Z-Group" to -- Influence of the Z-group --.

Item (30) Foreign Application Priority Date, please add -- August 3, 2016 (JP)...JP2016-152825 --.

In the Specification

At Column 11, Lines 63-64, please change "co-(meth)acryloyl(poly)oxyethylenephosphorylcholine," to -- ω-(meth)acryloyl(poly)oxyethylene phosphorylcholine, --.

In the Claims

At Column 68, Line 37 (Claim 13), please change "a isobutyl" to -- an isobutyl --.

Signed and Sealed this
Twenty-third Day of November, 2021

Drew Hirshfeld
*Performing the Functions and Duties of the
Under Secretary of Commerce for Intellectual Property and
Director of the United States Patent and Trademark Office*